(12) United States Patent
Aihara et al.

(10) Patent No.: US 9,252,368 B2
(45) Date of Patent: Feb. 2, 2016

(54) CYCLIC AZINE COMPOUND HAVING NITROGEN-CONTAINING CONDENSED AROMATIC GROUP, METHOD FOR PRODUCING SAME, AND ORGANIC ELECTROLUMINESCENT DEVICE COMPRISING SAME AS CONSTITUENT COMPONENT

(71) Applicants: TOSOH CORPORATION, Yamaguchi (JP); SAGAMI CHEMICAL RESEARCH INSTITUTE, Kanagawa (JP)

(72) Inventors: Hidenori Aihara, Kanagawa (JP); Yuji Oka, Kanagawa (JP); Keisuke Nomura, Kanagawa (JP); Tsuyoshi Tanaka, Kanagawa (JP); Naoki Uchida, Kanagawa (JP)

(73) Assignees: TOSOH CORPORATION, Yamaguchi (JP); SAGAMI CHEMICAL RESEARCH INSTITUTE, Kanagawa (JP)

( * ) Notice: Subject to any disclaimer, the term of this patent is extended or adjusted under 35 U.S.C. 154(b) by 0 days.

(21) Appl. No.: 14/357,396

(22) PCT Filed: Nov. 9, 2012

(86) PCT No.: PCT/JP2012/079092
§ 371 (c)(1),
(2) Date: May 9, 2014

(87) PCT Pub. No.: WO2013/069762
PCT Pub. Date: May 16, 2013

(65) Prior Publication Data
US 2014/0330013 A1    Nov. 6, 2014

(30) Foreign Application Priority Data

Nov. 11, 2011 (JP) .................................. 2011-248080
Nov. 1, 2012 (JP) .................................. 2012-241811

(51) Int. Cl.
| | |
|---|---|
| C07D 251/24 | (2006.01) |
| C09K 11/06 | (2006.01) |
| H01L 51/52 | (2006.01) |
| H01L 51/54 | (2006.01) |
| C07D 401/04 | (2006.01) |

(Continued)

(52) U.S. Cl.
CPC .......... H01L 51/0052 (2013.01); C07D 251/24 (2013.01); C07D 401/10 (2013.01); C07D 401/14 (2013.01); C07D 471/04 (2013.01); C07D 519/00 (2013.01); H01L 51/0067 (2013.01); H01L 51/0069 (2013.01); H01L 51/5072 (2013.01); H01L 51/0072 (2013.01)

(58) Field of Classification Search
CPC .. C07D 251/24; C07D 401/04; C07D 401/10; C07D 401/14; C07D 403/04; C07D 403/10; C07D 403/14; C09K 11/06; H05B 33/14; H01L 51/0032; H01L 51/5064; H01L 51/5032
USPC ................................. 544/180; 345/82, 76, 75
See application file for complete search history.

(56) References Cited

U.S. PATENT DOCUMENTS

| | | |
|---|---|---|
| 6,656,608 B1 | 12/2003 | Kita et al. |
| 7,994,316 B2 | 8/2011 | Yamakawa et al. |

(Continued)

FOREIGN PATENT DOCUMENTS

| | | |
|---|---|---|
| EP | 1724323 A1 | 11/2006 |
| EP | 1962354 A1 | 8/2008 |

(Continued)

OTHER PUBLICATIONS

International Search Report in PCT/JP2012/079092 on Jan. 8, 2013.
Ishiyama et. al., Journal of Organic Chemistry vol. 60, No. 23, dated Jul. 10, 1995, p. 7508-7510, "Palladium(0)-Catalyzed Cross-Coupling Reaction of Alkoxydiboron with Haloarenes: A Direct Procedure for Arylboronic Esters."
Murata et. al., Journal of Organic Chemistry vol. 65, No. 1, dated Dec. 17, 1999, p. 164-168, "Palladium-Catalyzed Borylation of Aryl Halides Triflates with Dialkoxyborane: A Novel and Facile Synthetic Route to Arylboronates."
Partial European search report issued with respect to application No. 12847767.6, mail date is Jun. 15, 2015.

*Primary Examiner* — Venkataraman Balasubramanian
(74) *Attorney, Agent, or Firm* — Greenblum & Bernstein, P.L.C.

(57) ABSTRACT

A cyclic azine compound of formula (1):

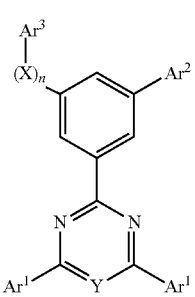

(1)

wherein, Y is C—H or a nitrogen atom, $Ar^1$ is a $C_{6-18}$ aromatic hydrocarbon group, which may be substituted with an $C_{1-4}$ alkyl group or a phenyl group, $Ar^2$ is a hydrogen atom, or a $C_{6-18}$ aromatic hydrocarbon group, which may be substituted with a phenyl group or a pyridyl group, or is a nitrogen-containing condensed ring $C_{9-15}$ aromatic group, $Ar^3$ is a nitrogen-containing condensed ring $C_{9-15}$ aromatic group, X is a phenylene group, and n is an integer in the range of 0-3. The cyclic azine compound is useful as a constituent of an organic electroluminescent device.

11 Claims, 1 Drawing Sheet

(51) Int. Cl.

| | |
|---|---|
| *C07D 401/10* | (2006.01) |
| *C07D 401/14* | (2006.01) |
| *C07D 403/04* | (2006.01) |
| *C07D 403/10* | (2006.01) |
| *C07D 403/14* | (2006.01) |
| *H05B 33/14* | (2006.01) |
| *H01L 51/00* | (2006.01) |
| *C07D 471/04* | (2006.01) |
| *C07D 519/00* | (2006.01) |
| *H01L 51/50* | (2006.01) |

(56) References Cited

U.S. PATENT DOCUMENTS

| | | |
|---|---|---|
| 8,268,997 B2 | 9/2012 | Yamakawa et al. |
| 8,569,485 B2 | 10/2013 | Yamakawa et al. |
| 8,674,091 B2 | 3/2014 | Aihara et al. |
| 8,735,577 B2 | 5/2014 | Aihara et al. |
| 2004/0058195 A1 | 3/2004 | Kita et al. |
| 2004/0062951 A1 | 4/2004 | Kita et al. |
| 2004/0072019 A1 | 4/2004 | Kita et al. |
| 2004/0096696 A1 | 5/2004 | Kita et al. |
| 2006/0025564 A1 | 2/2006 | Schafer et al. |
| 2006/0154105 A1 | 7/2006 | Yamamoto et al. |
| 2007/0020485 A1 | 1/2007 | Kita et al. |
| 2007/0190355 A1* | 8/2007 | Ikeda et al. .................... 428/690 |
| 2007/0257600 A1* | 11/2007 | Matsuura et al. ............. 313/498 |
| 2008/0199726 A1 | 8/2008 | Schafer et al. |
| 2010/0163857 A1 | 7/2010 | Kim et al. |
| 2010/0249406 A1 | 9/2010 | Yamakawa et al. |
| 2011/0156013 A1 | 6/2011 | Kim et al. |
| 2011/0190494 A1 | 8/2011 | Aihara et al. |
| 2011/0284832 A1 | 11/2011 | In et al. |
| 2011/0288295 A1 | 11/2011 | Aihara et al. |
| 2012/0126690 A1 | 5/2012 | Ise et al. |
| 2012/0214993 A1 | 8/2012 | Aihara et al. |
| 2012/0235123 A1 | 9/2012 | Lee et al. |

FOREIGN PATENT DOCUMENTS

| | | |
|---|---|---|
| EP | 2141158 A1 | 1/2010 |
| EP | 2468731 A1 | 6/2012 |
| JP | 2001/143869 | 5/2001 |
| JP | 2003/45662 | 2/2003 |
| JP | 2004/002297 | 1/2004 |
| JP | 2004/022334 | 1/2004 |
| JP | 2004/031004 | 1/2004 |
| JP | 2006/510732 | 3/2006 |
| JP | 2007/137829 | 6/2007 |
| JP | 2007/534722 | 11/2007 |
| JP | 2008/280330 | 11/2008 |
| JP | 2009/021336 | 1/2009 |
| JP | 2010/090034 | 4/2010 |
| JP | 2010/106018 | 5/2010 |
| WO | 2004/039786 | 5/2004 |
| WO | 2005/076669 | 8/2005 |
| WO | 2005/085387 | 9/2005 |
| WO | 2005/105950 | 11/2005 |
| WO | 2007/069569 | 6/2007 |
| WO | 2009/031855 | 3/2009 |
| WO | 2010/064627 | 6/2010 |
| WO | 2010/076986 | 7/2010 |
| WO | 2011/013783 | 2/2011 |
| WO | 2011/013843 | 2/2011 |
| WO | 2011/019156 | 2/2011 |
| WO | 2011/021689 | 2/2011 |
| WO | 2011/099718 | 8/2011 |

* cited by examiner

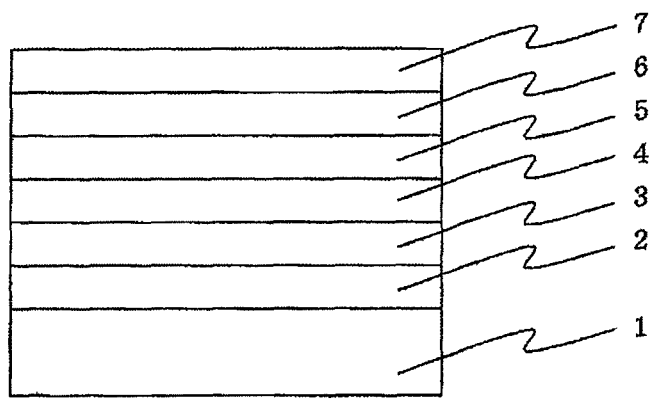

CYCLIC AZINE COMPOUND HAVING NITROGEN-CONTAINING CONDENSED AROMATIC GROUP, METHOD FOR PRODUCING SAME, AND ORGANIC ELECTROLUMINESCENT DEVICE COMPRISING SAME AS CONSTITUENT COMPONENT

TECHNICAL FIELD

This invention relates to a cyclic azine compound and a process for producing the cyclic azine compound.

The cyclic azine compound of the present invention has good electron transport characteristics and forms a stable film. Therefore, the cyclic azine compound is useful as a constituent used for an phosphorescent or fluorescent organic electroluminescent device.

This invention further relates to an organic electroluminescent device (hereinafter abbreviated to as "organic EL device" when appropriate) having at least one organic compound layer comprising the cyclic azine compound, which device exhibits improved drivability and luminescent characteristics with enhanced efficiency.

BACKGROUND ART

An organic EL device has a multilayer structure comprising (i) a light emitting layer comprising a luminescent material and (ii) a hole transport layer and an electron transport layer, which sandwich the luminescent layer, and (iii) an anode and a cathode, which sandwich the hole transport layer, the luminescent layer and the electron transport layer.

The organic EL device utilizes light emission (fluorescence or phosphorescence) occurring at deactivation of an exciton formed by the recombination of electron and hole, which are injected in the luminescent layer. The organic EL device is widely used for a display and other applications.

The cyclic azine compound according to the present invention includes both of a 1,3,5-triazine compound and a pyrimidine compound. The 1,3,5-triazine compound is novel and characterized as having a nitrogen-containing condensed ring aromatic group which is bonded, directly or via a phenylene group, to a phenyl group bonded on 2-position of a triazine ring. The pyrimidine compound also is novel and characterized as having a nitrogen-containing condensed ring aromatic group which is bonded, directly or via a phenylene group, to a phenyl group bonded on 2-position of a pyrimidine ring.

Examples of an organic EL device comprising a 1,3,5-triazine compound as a constituent are disclosed in patent document 1. This 1,3,5-triazine compound does not have a nitrogen-containing condensed ring aromatic group, and therefore, this compound is distinguished from the 1,3,5-triazine compound of the present invention.

1,3,5-triazine derivatives are disclosed in patent document 2. These 1,3,5-triazine derivatives include those which have a 1,3,5-triazine ring and a nitrogen-containing aromatic group. However, no working examples are given wherein specific examples of such 1,3,5-triazine derivatives are described.

As an example of a 1,3,5-triazine compound which is useful as a constituent of an organic EL device, a triazine compound having two phenanthrolinyl groups is known (see, for example, patent document 3) and a triazine compound having two isoquinolinyl groups is known (see, for example, patent document 4). These triazine compounds have a structure such that two nitrogen-containing condensed ring aromatic groups are symmetrically arranged via an arylene group on a phenyl group bonded to 2-position of the triazine ring, and therefore, this compound is distinguished from the 1,3,5-triazine compound of the present invention.

PRIOR ART DOCUMENTS

Patent Document

Patent document 1: JP 2004-022334 A
Patent document 2: JP 2007-137829 A
Patent document 3: JP 2010-090034 A
Patent document 4: JP 2010-106018 A

SUMMARY OF THE INVENTION

Problems to be Solved by the Invention

In general, an electron transport material used for an organic EL device is poor in durability as compared with a hole transport material, and an organic EL device comprising the electron transport material has a short life. Only few electron transport materials give an organic EL device having a long life. A satisfactory electron transport material having good durability and giving an organic EL device exhibiting a low voltage drivability and a reduced power consumption cannot be found in the conventional electron transport materials. Thus, a novel electron transport material having the satisfactory properties is eagerly desired.

Means for Solving the Problems

The present inventors made extensive researches to solve the above-mentioned problems, and found that a cyclic azine compound having a structure such that a nitrogen-containing condensed ring aromatic group having 9 to 15 carbon atoms is bonded, directly or via a phenylene group, to a phenyl group bonded on 2-position of the triazine ring has a high glass transition temperature (Tg), and is capable of forming a stable amorphous film by vacuum deposition.

Further, it has been found that an organic EL device having an electron transport layer comprising the above-mentioned cyclic triazine compound exhibits a long life, and a reduced power consumption as compared with the widely used organic EL devices. Based on these findings, the present invention has been completed.

In one aspect of the present invention, there is provided a cyclic azine compound represented by the general formula (1):

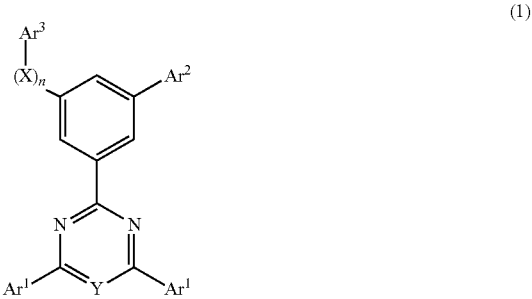

In the formula (1),
Y represents C—H or a nitrogen atom,
$Ar^1$ represents an aromatic hydrocarbon group having 6 to 18 carbon atoms, which may be substituted with an alkyl group having 1 to 4 carbon atoms or a phenyl group, Ar² represents a hydrogen atom, or an aromatic hydrocarbon group having 6 to 18 carbon atoms, which may be substituted with a phenyl group or a pyridyl group, or Ar² represents a nitrogen-containing condensed ring aromatic group having 9 to 15 carbon atoms, Ar³ represents a nitrogen-containing condensed ring aromatic group having 9 to 15 carbon atoms, X represents a phenylene group, and n represents an integer in the range of 0 to 3.

In another aspect of the present invention, there is provided a process for producing a cyclic azine compound represented by the general formula (1):

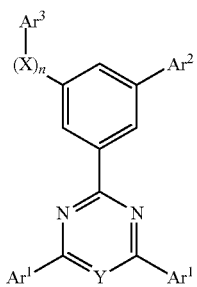

(1)

In the formula (1),

Y represents C—H or a nitrogen atom,

Ar¹ represents an aromatic hydrocarbon group having 6 to 18 carbon atoms, which may be substituted with an alkyl group having 1 to 4 carbon atoms or a phenyl group, Ar² represents a hydrogen atom, or an aromatic hydrocarbon group having 6 to 18 carbon atoms, which may be substituted with a phenyl group or a pyridyl group, or Ar² represents a nitrogen-containing condensed ring aromatic group having 9 to 15 carbon atoms, Ar³ represents a nitrogen-containing condensed ring aromatic group having 9 to 15 carbon atoms, X represents a phenylene group, and n represents an integer in the range of 0 to 3.

Said process is characterized by coupling a compound represented by the following general formula (2) with a compound represented by the following general formula (3) in the presence of a base and a palladium catalyst or in the presence of a base, a palladium catalyst and an alkali metal salt.

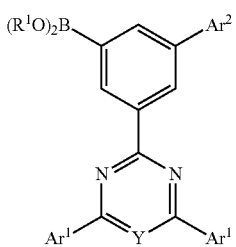

(2)

In the formula (2),

Y represents C—H or a nitrogen atom,

Ar¹ represents an aromatic hydrocarbon group having 6 to 18 carbon atoms, which may be substituted with an alkyl group having 1 to 4 carbon atoms or a phenyl group, Ar² represents a hydrogen atom, or an aromatic hydrocarbon group having 6 to 18 carbon atoms, which may be substituted with a phenyl group or a pyridyl group, or Ar² represents a nitrogen-containing condensed ring aromatic group having 9 to 15 carbon atoms, and R¹ represents a hydrogen atom, an alkyl group having 1 to 3 carbon atoms or a phenyl group, provided that two R¹'s in the B(OR¹)₂ may be the same or different, and the two R¹'s may form a ring together with the two oxygen atoms and the boron atom.

In the formula (3),

Ar³ represents a nitrogen-containing condensed ring aromatic group having 9 to 15 carbon atoms, X represents a phenylene group, n represents an integer in the range of 0 to 3, and Z¹ represents a leaving group.

In a still another aspect of the present invention, there is provided a process for producing a cyclic azine compound represented by the general formula (1):

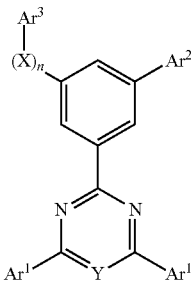

(1)

In the formula (3),

Y represents C—H or a nitrogen atom,

Ar¹ represents an aromatic hydrocarbon group having 6 to 18 carbon atoms, which may be substituted with an alkyl group having 1 to 4 carbon atoms or a phenyl group, Ar² represents a hydrogen atom, or an aromatic hydrocarbon group having 6 to 18 carbon atoms, which may be substituted with a phenyl group or a pyridyl group, or Ar² represents a nitrogen-containing condensed ring aromatic group having 9 to 15 carbon atoms, Ar³ represents a nitrogen-containing condensed ring aromatic group having 9 to 15 carbon atoms, X represents a phenylene group, and n represents an integer in the range of 0 to 3.

Said process is characterized by coupling a compound represented by the following general formula (8) with a compound represented by the following general formula (9) in the presence of a base and a palladium catalyst or in the presence of a base, a palladium catalyst and an alkali metal salt.

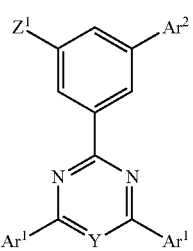

(8)

In the formula (8),

Y represents C—H or a nitrogen atom,

Ar¹ represents an aromatic hydrocarbon group having 6 to 18 carbon atoms, which may be substituted with an alkyl group having 1 to 4 carbon atoms or a phenyl group, Ar² represents a hydrogen atom, or an aromatic hydrocarbon group having 6 to 18 carbon atoms, which may be substituted with a phenyl group or a pyridyl group, or Ar² represents a nitrogen-containing condensed ring aromatic group having 9 to 15 carbon atoms, and $Z^1$ represents a chlorine atom or a bromine atom.

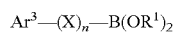
(9)

In the formula (9), $Ar^3$ represents a nitrogen-containing condensed ring aromatic group having 9 to 15 carbon atoms, X represents a phenylene group, n represents an integer in the range of 0 to 3, and $R^1$ represents a hydrogen atom, an alkyl group having 1 to 3 carbon atoms or a phenyl group, provided that two $R^1$s in the $B(OR^1)_2$ may be the same or different, and the two $R^1$s may form a ring together with the two oxygen atoms and the boron atom.

In a further aspect of the present invention, there is provided a process for producing a cyclic azine compound represented by the general formula (1'):

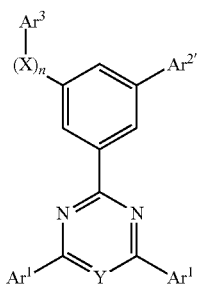
(1')

In the formula (1'),

Y represents C—H or a nitrogen atom, $Ar^1$ represents an aromatic hydrocarbon group having 6 to 18 carbon atoms, which may be substituted with an alkyl group having 1 to 4 carbon atoms or a phenyl group, $Ar^{2'}$ represents an aromatic hydrocarbon group having 6 to 18 carbon atoms, which may be substituted with a phenyl group or a pyridyl group, or $Ar^{2'}$ represents a nitrogen-containing condensed ring aromatic group having 9 to 15 carbon atoms, $Ar^3$ represents a nitrogen-containing condensed ring aromatic group having 9 to 15 carbon atoms, X represents a phenylene group, and n represents an integer in the range of 0 to 3.

Said process for producing the compound of the formula (1') is characterized by coupling a compound represented by the following general formula (12) with a compound represented by the following general formula (13) in the presence of a base and a palladium catalyst or in the presence of a base, a palladium catalyst and an alkali metal salt.

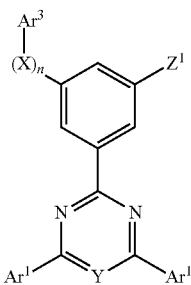
(12)

In the formula (12),

Y represents C—H or a nitrogen atom, $Ar^1$ represents an aromatic hydrocarbon group having 6 to 18 carbon atoms, which may be substituted with an alkyl group having 1 to 4 carbon atoms or a phenyl group, $Ar^3$ represents a nitrogen-containing condensed ring aromatic group having 9 to 15 carbon atoms, X represents a phenylene group, n represents an integer in the range of 0 to 3, and $Z^1$ represents a chlorine atom or a bromine atom.

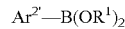
(13)

In the formula (13), $Ar^{2'}$ represents an aromatic hydrocarbon group having 6 to 18 carbon atoms, which may be substituted with a phenyl group or a pyridyl group, or $Ar^{2'}$ represents a nitrogen-containing condensed ring aromatic group having 9 to 15 carbon atoms, $R^1$ represents a hydrogen atom, an alkyl group having 1 to 3 carbon atoms or a phenyl group, provided that two $R^1$s in the $B(OR^1)_2$ may be the same or different, and the two $R^1$s may form a ring together with the two oxygen atoms and the boron atom.

In a further aspect of the present invention, there is provided an organic electroluminescent device characterized by comprising, as a constituent, a cyclic azine compound represented by the general formula (1):

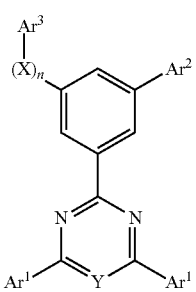
(1)

In the formula (1),

Y represents C—H or a nitrogen atom, $Ar^1$ represents an aromatic hydrocarbon group having 6 to 18 carbon atoms, which may be substituted with an alkyl group having 1 to 4 carbon atoms or a phenyl group, $Ar^2$ represents a hydrogen atom, or an aromatic hydrocarbon group having 6 to 18 carbon atoms, which may be substituted with a phenyl group or a pyridyl group, or $Ar^2$ represents a nitrogen-containing condensed ring aromatic group having 9 to 15 carbon atoms, Ar³ represents a nitrogen-containing condensed ring aromatic group having 9 to 15 carbon atoms, X represents a phenylene group, and n represents an integer in the range of 0 to 3.

Effect of the Invention

The cyclic azine compound of the present invention has a high Tg and is capable of forming a stable amorphous film. Further, this compound exhibits good electron injection and electron transport characteristics as a material for an organic EL device.

Therefore, the cyclic azine compound of the present invention is useful as a material, especially an electron transport material, for an organic EL device. An organic EL device comprising as a constituent the cyclic azine compound of the present invention is characterized as having a long life and exhibiting a low drive voltage.

BRIEF DESCRIPTION OF THE DRAWINGS

FIG. 1 is a cross-sectional view of an organic EL device made in Test Example 1.

EXPLANATION OF REFERENCE NUMERALS

1. Glass substrate with a transparent ITO electrode
2. Hole injection layer
3. Hole transport layer
4. Emitting layer
5. Hole blocking layer
6. Electron transport layer
7. Anode layer

MODE FOR PRACTICING THE INVENTION

The present invention will be described specifically and in detail.

In the formula (1) representing the cyclic azine compound of the present invention, an aromatic hydrocarbon group having 6 to 18 carbon atoms represented by Ar¹ includes, for example, a phenyl group, a naphthyl group, an anthranyl group, a perylenyl group and a triphenylenyl group. These aromatic hydrocarbon groups may be substituted with an alkyl group having 1 to 4 carbon atoms or a phenyl group. The alkyl group as a substituent may be any of straight, branched and cyclic alkyl groups, and the alkyl group may be substituted with at least one halogen atom or other substituent. The phenyl group as a substituent may also be substituted with at least one halogen atom or other substituent.

As specific examples of Ar¹, there can be mentioned the following substituted and unsubstituted aromatic hydrocarbon groups, but, Ar¹ should not be limited thereto.

As specific examples of the unsubstituted phenyl group and the phenyl groups substituted with an alkyl group having 1 to 4 carbon atoms or a phenyl group, there can be mentioned a phenyl group, and substituted phenyl groups such as p-tolyl, m-tolyl, o-tolyl, 4-trifluoromethylphenyl, 3-trifluoromethylphenyl, 2-trifluoromethylphenyl, 2,4-dimethylphenyl, 3,5-dimethylphenyl, 2,6-dimethylphenyl, mesityl, 2-ethylphenyl, 3-ethylphenyl, 4-ethylphenyl, 2,4-diethylphenyl, 3,5-diethylphenyl, 2-propylphenyl, 3-propylphenyl, 4-propylphenyl, 2,4-dipropylphenyl, 3,5-dipropylphenyl, 2-isopropylphenyl, 3-isopropylphenyl, 4-isopropylphenyl, 2,4-diisopropylphenyl, 3,5-diisopropylphenyl, 2-butylphenyl, 3-butylphenyl, 4-butylphenyl, 2,4-dibutylphenyl, 3,5-dibutylphenyl, 2-tert-butylphenyl, 3-tert-butylphenyl, 4-tert-butylphenyl, 2,4-di-tert-butylphenyl and 3,5-di-tert-butylphenyl groups;

4-biphenylyl, 3-biphenylyl and 2-biphenylyl groups, and substituted biphenylyl groups such as 2-methylbiphenyl-4-yl, 3-methylbiphenyl-4-yl, 2'-methylbiphenyl-4-yl, 4'-methylbiphenyl-4-yl, 2,2'-dimethylbiphenyl-4-yl, 2',4',6'-trimethylbiphenyl-4-yl, 6-methylbiphenyl-3-yl, 5-methylbiphenyl-3-yl, 2'-methylbiphenyl-3-yl, 4'-methylbiphenyl-3-yl, 6,2'-dimethylbiphenyl-3-yl, 2',4',6'-trimethylbiphenyl-3-yl, 5-methylbiphenyl-2-yl, 6-methylbiphenyl-2-yl, 2'-methylbiphenyl-2-yl, 4'-methylbiphenyl-2-yl, 6,2'-dimethylbiphenyl-2-yl, 2',4',6'-trimethylbiphenyl-2-yl, 2-trifluoromethylbiphenyl-4-yl, 3-trifluoromethylbiphenyl-4-yl, 2'-trifluoromethylbiphenyl-4-yl, 4'-trifluoromethylbiphenyl-4-yl, 6-trifluoromethylbiphenyl-3-yl, 5-trifluoromethylbiphenyl-3-yl, 2'-trifluoromethylbiphenyl-3-yl, 4'-trifluoromethylbiphenyl-3-yl, 5-trifluoromethylbiphenyl-2-yl, 6-trifluoromethylbiphenyl-2-yl, 2'-trifluoromethylbiphenyl-2-yl, 4'-trifluoromethylbiphenyl-2-yl, 3-ethylbiphenyl-4-yl, 4'-ethylbiphenyl-4-yl, 2',4',6'-triethylbiphenyl-4-yl, 6-ethylbiphenyl-3-yl, 4'-ethylbiphenyl-3-yl, 5-ethylbiphenyl-2-yl, 4'-ethylbiphenyl-2-yl, 2',4',6'-triethylbiphenyl-2-yl, 3-propylbiphenyl-4-yl, 4'-propylbiphenyl-4-yl, 2',4',6'-tripropylbiphenyl-4-yl, 6-propylbiphenyl-3-yl, 4'-propylbiphenyl-3-yl, 5-propylbiphenyl-2-yl, 4'-propylbiphenyl-2-yl, 2',4',6'-tripropylbiphenyl-2-yl, 3-isopropylbiphenyl-4-yl, 4'-isopropylbiphenyl-4-yl, 2',4',6'-triisopropylbiphenyl-4-yl, 6-isopropylbiphenyl-3-yl, 4'-isopropylbiphenyl-3-yl, 5-isopropylbiphenyl-2-yl, 4'-isopropylbiphenyl-2-yl, 2',4',6'-triisopropylbiphenyl-2-yl, 3-butylbiphenyl-4-yl, 4'-butylbiphenyl-4-yl, 2',4',6'-tributylbiphenyl-4-yl, 6-butylbiphenyl-3-yl, 4'-butylbiphenyl-3-yl, 5-butylbiphenyl-2-yl, 4'-butylbiphenyl-2-yl, 2',4',6'-tributylbiphenyl-2-yl, 3-tert-butylbiphenyl-4-yl, 4'-tert-butylbiphenyl-4-yl, 2',4',6'-tri-tert-butylbiphenyl-4-yl, 6-tert-butylbiphenyl-3-yl, 4'-tert-butylbiphenyl-3-yl, 5-tert-butylbiphenyl-2-yl, 4'-tert-butylbiphenyl-2-yl and 2',4',6'-tri-tert-butylbiphenyl-2-yl groups; and terphenylyl groups such as 1,1':4',1"-terphenyl-3-yl, 1,1':4',1"-terphenyl-4-yl, 1,1':3',1"-terphenyl-3-yl, 1,1':3',1"-terphenyl-4-yl, 1,1':3',1"-terphenyl-5'-yl, 1,1':2',1"-terphenyl-3-yl, 1,1':2',1"-terphenyl-4-yl and 1,1':2',1"-terphenyl-4'-yl groups.

Of the above-listed unsubstituted and substituted phenyl groups, a phenyl group, a p-tolyl group, a m-tolyl group, an o-tolyl group, a 2,6-dimethylphenyl group, a 4-tert-butylphenyl group, a 4-biphenylyl group, a 3-biphenylyl group, a 2-biphenylyl group, a 1,1':4',1"-terphenyl-4-yl group, a 1,1':2',1"-terphenyl-4-yl group and a 1,1':3',1"-terphenyl-5'-yl group are preferable in view of the performance as a material for an organic EL device.

In view of ease in synthesis, a phenyl group, a p-tolyl group, a 4-tert-butylphenyl group, a 4-biphenylyl group and a 3-biphenylyl group are more preferable.

As specific examples of unsubstituted naphthyl groups, and naphthyl groups substituted with an alkyl group having 1 to 4 carbon atoms or a phenyl group, there can be mentioned a 1-naphthyl group and 2-naphthyl group, and substituted naphthyl groups such as 4-methylnaphthanen-1-yl, 4-trifluoromethylnaphthanen-1-yl, 4-ethylnaphthanen-1-yl, 4-propylnaphthanen-1-yl, 4-butylnaphthanen-1-yl, 4-tert-butylnaphthanen-1-yl, 5-methylnaphthanen-1-yl, 5-trifluoromethylnaphthanen-1-yl, 5-ethylnaphthanen-1-yl, 5-propylnaphthanen-1-yl, 5-butylnaphthanen-1-yl, 5-tert-butylnaphthanen-1-yl, 6-methylnaphthanen-2-yl, 6-trifluoromethylnaphthanen-2-yl, 6-ethylnaphthanen-2-yl, 6-propylnaphthanen-2-yl, 6-butylnaphthanen-2-yl, 6-tert-butylnaphthanen-2-yl, 7-methylnaphthanen-2-yl, 7-trifluoromethylnaphthanen-2-yl, 7-ethylnaphthanen-2-yl, 7-propylnaphthanen-2-yl, 7-butylnaphthanen-2-yl, 7-tert-butylnaphthanen-2-yl, 2-phenylnaphthanen-1-yl, 3-phenyl-naphthanen-1-yl, 4-phenylnaphthanen-1-yl, 5-phenylnaph-thanen-1-yl, 6-phenylnaphthanen-1-yl, 7-phenylnaphthanen-1-yl, 8-phenylnaphthanen-1-yl, 1-phenylnaphthanen-2-yl, 2,4-diphenylnaphthanen-1-yl, 4,6-diphenylnaphthanen-1-yl, 5,7-diphenylnaphthanen-1-yl, 1,3-diphenylnaphthanen-2-yl, 4,7-diphenylnaphthanen-2-yl, 5,8-diphenylnaphthanen-2-yl, 5,6,7,8-tetraphenylnaphthanen-1-yl and 5,6,7,8-tetraphenyl-naphthanen-2-yl groups.

Of the above-listed unsubstituted and substituted naphthyl groups, a 1-naphthyl group, a 4-methylnaphthalen-1-yl group, a 4-tert-butylnaphthalen-1-yl group, a 5-methylnaph-thalen-1-yl group, a 5-tert-butylnaphthalen-1-yl group, a 4-phenylnaphthalen-1-yl group, a 2-naphthyl group, a 6-me-thylnaphthalen-2-yl group, a 6-tert-butylnaphthalen-2-yl group, a 7-methylnaphthalen-2-yl group and a 7-tert-butyl-naphthalen-2-yl group are preferable in view of the perfor-mance as a material for an organic EL device. In view of ease in synthesis, 2-naphthyl group is especially preferable.

As specific examples of the unsubstituted anthracenyl groups and the anthracenyl groups substituted with an alkyl group having 1 to 4 carbon atoms or a phenyl group, the unsubstituted perylenyl groups and the perylenyl groups sub-stituted with an alkyl group having 1 to 4 carbon atoms or a phenyl group, and the unsubstituted triphenylenyl groups and the triphenylenyl groups substituted with an alkyl group hav-ing 1 to 4 carbon atoms or a phenyl group, there can be mentioned a 1-anthracenyl group, a 2-anthracenyl group, a 9-anthracenyl group, a 1-perylenyl group, a 2-perylenyl group and a 1-triphenylenyl group.

In the general formula (1) representing the cyclic azine compound according to the present invention, $Ar^2$ represents a hydrogen atom, or an aromatic hydrocarbon group having 6 to 18 carbon atoms, which may be substituted with a phenyl group or a pyridyl group, or $Ar^2$ represents a nitrogen-con-taining condensed ring aromatic group having 9 to 15 carbon atoms.

The aromatic hydrocarbon group having 6 to 18 carbon atoms represented by $Ar^2$ includes, for example, a phenyl group, a biphenylyl group, a naphthyl group, an anthranyl group, a phenanthrenyl group, a perylenyl group, a triph-enylenyl group and a pyrenyl group. These aromatic hydro-carbon groups may be substituted with a phenyl group or a pyridyl group.

Of these, a phenyl group, a biphenylyl group and a phenan-threnyl group are preferable in view of the performance as a material for an organic EL device. These groups may be substituted with a phenyl group or a pyridyl group.

As specific examples of the unsubstituted phenyl group, the phenyl groups substituted with a phenyl group or a pyridyl group, the unsubstituted biphenylyl group, and the biphenylyl groups substituted with a phenyl group or a pyridyl group, there can be mentioned 2-(2-pyridyl)phenyl, 3-(2-pyridyl) phenyl, 4-(2-pyridyl)phenyl, 2-(3-pyridyl)phenyl, 3-(3-py-ridyl)phenyl, 4-(3-pyridyl)phenyl, 2-(4-pyridyl)phenyl, 3-(4-pyridyl)phenyl, 4-(4-pyridyl)phenyl, 2,4-bis(2-pyridyl) phenyl, 2,6-bis(2-pyridyl)phenyl, 3,4-bis(2-pyridyl)phenyl, 2,4,6-tris(2-pyridyl)phenyl, 4-biphenylyl, 3-biphenylyl, 2-biphenylyl, 1,1':4',1''-terphenyl-3-yl, 1,1':4',1''-terphenyl-4-yl, 1,1':3',1''-terphenyl-3-yl, 1,1':3',1''-terphenyl-4-yl, 1,1': 3',1''-terphenyl-5'-yl, 1,1':2',1''-terphenyl-3-yl, 1,1':2',1''-ter-phenyl-4-yl, 1,1':2',1''-terphenyl-4'-yl, 2'-(2-pyridyl) biphenyl-4-yl, 3'-(2-pyridyl)biphenyl-4-yl, 4'-(2-pyridyl) biphenyl-4-yl, 2'-(3-pyridyl)biphenyl-4-yl, 3'-(3-pyridyl) biphenyl-4-yl, 4'-(3-pyridyl)biphenyl-4-yl, 2'-(4-pyridyl) biphenyl-4-yl, 3'-(4-pyridyl)biphenyl-4-yl, 4'-(4-pyridyl) biphenyl-4-yl, 2'-(2-pyridyl)biphenyl-3-yl, 3'-(2-pyridyl) biphenyl-3-yl, 4'-(2-pyridyl)biphenyl-3-yl, 2'-(3-pyridyl) biphenyl-3-yl, 3'-(3-pyridyl)biphenyl-3-yl, 4'-(3-pyridyl) biphenyl-3-yl, 2'-(4-pyridyl)biphenyl-3-yl, 3'-(4-pyridyl) biphenyl-3-yl, 4'-(4-pyridyl)biphenyl-3-yl, 2'-(2-pyridyl) biphenyl-2-yl, 3'-(2-pyridyl)biphenyl-2-yl, 4'-(2-pyridyl) biphenyl-2-yl, 2'-(3-pyridyl)biphenyl-2-yl, 3'-(3-pyridyl) biphenyl-2-yl, 4'-(3-pyridyl)biphenyl-2-yl, 2'-(4-pyridyl) biphenyl-2-yl, 3'-(4-pyridyl)biphenyl-2-yl, 4'-(4-pyridyl) biphenyl-2-yl, 5-(4-pyridyl)biphenyl-3-yl and 3',5'-bis(2-pyridyl)biphenyl-3-yl groups.

Of the above-listed groups, a phenyl group, a 4-biphenylyl group, a 3-biphenylyl group, a 2-biphenylyl group, a 3-(2-pyridyl)phenyl group, a 4-(2-pyridyl)phenyl group, a 1,1':4', 1''-terphenyl-4-yl group, a 1,1':2',1''-terphenyl-4-yl group, a 1,1':3',1''-terphenyl-5'-yl group, a 3'-(2-pyridyl)biphenyl-3-yl group, a 3'-(3-pyridyl)biphenyl-3-yl group, a 4'-(2-pyridyl) biphenyl-4-yl group, and a 4'-(3-pyridyl)biphenyl-4-yl group are preferable in view of the performance as a material for an organic EL device.

A phenyl group, a 4-biphenylyl group, a 3-biphenylyl group, a 4-(2-pyridyl)phenyl group, a 4'-(3-pyridyl)biphenyl-4-yl group are more preferable in view of ease in synthesis.

As specific examples of the unsubstituted naphthyl group and the naphthyl group substituted with a phenyl group or a pyridyl group, the unsubstituted anthranyl group and the anthranyl group substituted with a phenyl group or a pyridyl group, the unsubstituted perylenyl group and the perylenyl group substituted with a phenyl group or a pyridyl group, the unsubstituted phenanthrenyl group and the phenanthrenyl group substituted with a phenyl group or a pyridyl group, the unsubstituted triphenylenyl group and the triphenylenyl group substituted with a phenyl group or a pyridyl group, and the unsubstituted pyrenyl group and the pyrenyl group sub-stituted with a phenyl group or a pyridyl group, there can be mentioned a 1-naphthyl group, a 2-naphthyl group, a 1-an-thranyl group, a 2-anthranyl group, a 9-anthranyl group, a 1-phenanthrenyl group, a 2-phenanthrenyl group, a 3-phenanthrenyl group, a 9-phenanthrenyl group, a 1-peryle-nyl group, a 2-perylenyl group, a 1-triphenylenyl group, a 6-phenylnaphthalen-2-yl group, a 8-(2-pyridyl)naphthalen-2-yl group, a 10-phenylanthracene-9-yl group, a 10-(2-py-ridyl)anthracen-9-yl group, a 1-pyrenyl group and a 2-pyre-nyl group.

Of the above-listed groups, a 2-naphthyl group, a 9-anthra-nyl group, a 9-phenanthrenyl group, a 8-(2-pyridyl)naphtha-len-2-yl group and a 10-(2-pyridyl) anthracen-9-yl group are preferable in view of the performance of as a material for an organic EL device. A 9-anthranyl group and a 9-phenanthre-nyl group are especially preferable in view of ease in synthe-sis.

The nitrogen-containing condensed ring aromatic group having 9 to 15 carbon atoms represented by $Ar^2$ includes, for example, a quinolinyl group, an isoquinolinyl group, a phenanthrolinyl group, a naphthyridinyl group, a quinoxali-nyl group, a phenanthrolidinyl group and an acrydinyl group.

More specifically, as specific examples of the nitrogen-containing condensed ring aromatic group having 9 to 15 carbon atoms, represented by $Ar^2$, there can be mentioned a 2-quinolinyl group, a 8-quinolinyl group, a 1-isoquinolinyl group, a 3-isoquinolinyl group, a 4-isoquinolinyl group, a 5-isoquinolinyl group, a 6-isoquinolinyl group, a 7-isoquino-linyl group, a 8-isoquinolinyl group, a 2-naphthyridinyl group, a 2-quinoxalinyl group, a 6-phenanthrolidinyl group, a 9-acrydinyl group, a 2-phenanthrolinyl group, a 3-phenanthrolinyl group, a 4-phenanthrolinyl group and a 5-phenanthrolinyl group.

Of the above-listed groups, an isoquinolynyl group, a phenathrolinyl group and a quinolinyl group are preferable in view of the performance as a material for an organic EL device. More specifically, a 1-isoquinolinyl group, a 3-isoquinolinyl group, a 4-isoquinolinyl group, a 5-isoquinolinyl group, a 6-isoquinolinyl group, a 7-isoquinolinyl group, a 8-isoquinolinyl group, a 2-phenanthrolinyl group, a 3-phenanthrolinyl group, a 4-phenanthrolinyl group and a 5-phenanthrolinyl group, a 2-quinolinyl group, a 3-quinolinyl group, a 4-quinolinyl group, a 5-quinolinyl group, a 6-quinolinyl group, a 7-quinolinyl group and a 8-quinolinyl group are more preferable.

A 1-isoquinolinyl group, a 2-phenanthrolinyl group, a 5-phenanthrolinyl group and a 2-quinolinyl group are especially preferable in view of ease in synthesis.

In the general formula (1), $Ar^3$ represents a nitrogen-containing condensed ring aromatic group having 9 to 15 carbon atoms. As specific examples of the nitrogen-containing condensed ring aromatic group having 9 to 15 carbon atoms, those which are listed above as to $Ar^2$ can be mentioned.

Among the specific examples of the nitrogen-containing condensed ring aromatic group having 9 to 15 carbon atoms, listed above, isoquinolinyl groups, phenanthrolinyl groups and quinolinyl groups are preferable in view of the performance as a material for an organic EL device.

More specifically, a 1-isoquinolinyl group, a 3-isoquinolinyl group, a 4-isoquinolinyl group, a 5-isoquinolinyl group, a 6-isoquinolinyl group, a 7-isoquinolinyl group, a 8-isoquinolinyl group, a 2-phenanthrolinyl group, a 3-phenanthrolinyl group, a 4-phenanthrolinyl group, a 5-phenanthrolinyl group, a 2-quinolinyl group, a 3-quinolinyl group, a 4-quinolinyl group, a 5-quinolinyl group, a 6-quinolinyl group, a 7-quinolinyl group and a 8-quinolinyl group are more preferable.

A 1-isoquinolinyl group, a 2-phenanthrolinyl group, a 5-phenanthrolinyl group and a 2-quinolinyl group are especially preferable in view of the ease in synthesis.

In the formula (1), n represents an integer in the range of 0 to 3. n is preferably in the range of 0 to 2, more preferably an integer of 0 or 1.

When n is 0, $Ar^2$ and $Ar^3$ are preferably the same.

The invention will be described with regard to a process for producing the cyclic azine compound.

The cyclic azine compound of the present invention can be produced by a process including a step 1 represented by the reaction scheme illustrated below.

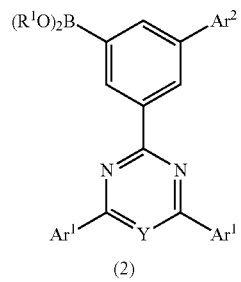

(2)

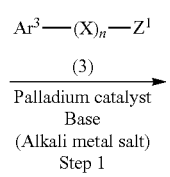

(3)

Palladium catalyst
Base
(Alkali metal salt)
Step 1

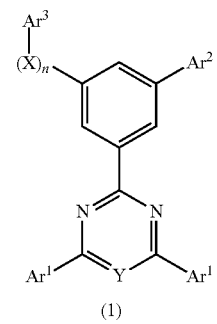

(1)

In the general formulas (2), (3) and (1), Y represents C—H or a nitrogen atom; and $Ar^1$ represents an aromatic hydrocarbon group having 6 to 18 carbon atoms, which may be substituted with an alkyl group having 1 to 4 carbon atoms or a phenyl group. $Ar^2$ represents a hydrogen atom, or an aromatic hydrocarbon group having 6 to 18 carbon atoms, which may be substituted with a phenyl group or a pyridyl group, or $Ar^2$ represents a nitrogen-containing condensed ring aromatic group having 9 to 15 carbon atoms. $R^1$ represents a hydrogen atom, an alkyl group having 1 to 3 carbon atoms or a phenyl group, provided that two $R^1$s in the $B(OR^1)_2$ may be the same or different, and the two $R^1$s may form a ring together with the two oxygen atoms and the boron atom. $Ar^3$ represents a nitrogen-containing condensed ring aromatic group having 9 to 15 carbon atoms; X represents a phenylene group; n represents an integer in the range of 0 to 3; and $Z^1$ represents a leaving group.

As specific examples of $B(OR^1)_2$ in the compound represented by the general formula (2) (abbreviated to as "compound (2)" when appropriate), there can be mentioned $B(OH)_2$, $B(OMe)_2$, $B(O(iso-Pr))_2$, $B(OBu)_2$ and $B(OPh)_2$.

When the two $R^1$s in the formula $B(OR^1)_2$ form a ring together with the boron atom bonded to the two $R^1$s via the two oxygen atoms, the formula $B(OR^1)_2$ includes, for example, the following groups (I) through (VI). Of these, the group represented by group (II) is preferable in view of high reaction yield.

(I)

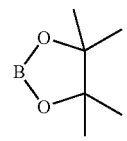

(II)

(III)

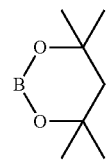

(IV)

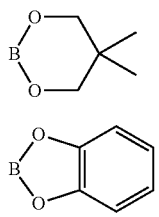

(V)

(VI)

The leaving group represented by $Z^1$ in the compound represented by the general formula (3) (abbreviated to as "compound (3)" when appropriate) is not particularly limited, and includes, for example, a chlorine atom, a bromine atom or a iodine atom. Of these, a bromine atom is preferable in view of high reaction yield.

Compound (3) can be prepared by the methods disclosed in, for example, Journal of Organic Chemistry, 2007, No. 72, 2318-2328; Org. Biomol. Chem., 2008, No. 6, 1320-1322; or JP 2008-280330, paragraphs [0061]-[0076].

The step 1 comprises a method of reacting compound (2) with compound (3) in the presence of a palladium catalyst and a base, or in the presence of a palladium catalyst, a base and an alkali metal salt to give the cyclic azine compound according to the present invention. This reaction can be effected with a high reaction yield of the target compound by adopting the reaction conditions in the general Suzuki-Miyaura reaction.

The palladium catalyst used in the step 1 includes, for example, palladium salts such as palladium chloride, palladium acetate, palladium trifluoroacetate and palladium nitrate; divalent palladium complexes such as palladium acetylacetonato, and π-allylpalladium chloride dimer; zero-valent palladium complexes such as bis(dibenzylideneacetone)palladium and tris(dibenzylideneacetone)dipalladium; and palladium complexes having a phosphine ligand such as dichlorobis(triphenylphosphine)palladium, tetrakis(triphenylphosphine)palladium and dichloro(1,1'-bis(diphenylphosphino)ferrocene)palladium. Of these, palladium complexes having tertiary phosphine as a ligand are preferable in view of high reaction yield. Especially, palladium complexes having triphenylphosphine as a ligand are more preferable in view of ease in availability and high reaction yield.

The amount of the palladium catalyst used in the step 1 may be a conventional catalytic amount and is not particularly limited, but the molar ratio of the palladium catalyst to compound (2) is preferably in the range of 1:5 to 1:200 in view of high reaction yield.

Palladium complex compounds having a tertiary phosphine as a ligand can also be synthesized in a reaction system containing a palladium salt, a divalent palladium complex or a zero-valent palladium complex and a tertiary phosphine or its salt added therein.

As specific examples of the tertiary phosphine used, there can be mentioned triphenylphosphine, trimethylphosphine, tributylphosphine, tri(tert-butyl)phosphine, tricyclohexylphosphine, tert-butyldiphenylphosphine, 9,9-dimethyl-4,5-bis(diphenylphosphino)xanthene, 2-(diphenylphosphino)-2'-(N,N-dimethylamino)biphenyl, 2-(di-tert-butylphosphino)biphenyl, 2-(dicyclohexylphosphino)biphenyl, bis(diphenylphosphino)methane, 1,2-bis(diphenylphosphino)ethane, 1,3-bis(diphenylphosphino)propane, 1,4-bis(diphenylphosphino)butane, 1'-bis(diphenylphosphino)ferrocene, tri(2-furyl)phosphine, tri(o-tolyl)phosphine, tris(2,5-xylyl)phosphine, (±)-2,2'-bis(diphenylphosphino)-1,1'-binaphthyl and 2-dicyclohexylphosphino-2',4',6'-triisopropylbiphenyl.

Of these, triphenylphosphine, 1,1'-bis(diphenylphosphino) ferrocene and tri(tert-butyl)phosphine are preferable in view of easy availability. Triphenylphosphine is most preferable in view of high reaction yield.

The molar ratio of the tertiary phosphine to the palladium salt or the palladium complex compound is preferably in the range of 1:10 to 10:1, and more preferably 1:2 to 3:1 in view of high reaction yield.

It is essential to carry out the reaction of step 1 in the presence of a base. The base capable of being used in the step 1 includes, for example, sodium hydroxide, potassium hydroxide, sodium carbonate, potassium carbonate, lithium carbonate, cesium carbonate, potassium acetate, sodium acetate, potassium phosphate and sodium phosphate. Of these, sodium carbonate, cesium carbonate and potassium phosphate are preferable in view of high reaction yield.

The molar ratio of the base to the compound (2) is not particularly limited, but is preferably in the range of 1:2 to 100:1, and more preferably 1:1 to 10:1 in view of high reaction yield.

The reaction of step 1 can also be carried out further in the presence of an alkali metal salt. The alkali metal salt capable of being used in the step 1 includes, for example, lithium fluoride, lithium chloride, lithium bromide, lithium iodide, sodium fluoride, sodium chloride, sodium bromide, sodium iodide, potassium fluoride, potassium chloride, potassium bromide, potassium iodide, rubidium fluoride, rubidium chloride, rubidium bromide, rubidium iodide, cesium fluoride, cesium chloride, cesium bromide and cesium iodide. Of these, lithium salts and potassium salts are preferable in view of high reaction yield and low cost. Lithium chloride and potassium chloride are especially preferable in view of very high reaction yield.

The molar ratio of the alkali metal salt the compound (2) is not particularly limited, but is preferably in the range of 1:2 to 100:1, and more preferably 1:1 to 10:1 in view of high reaction yield.

The molar ratio of the compound (3) to the compound (2), which are used in the step 1, is not particularly limited, but is preferably in the range of 1:1 to 5:1, and more preferably 2:1 to 3:1 in view of high reaction yield.

The reaction in the step 1 can be effected in a reaction medium. The reaction medium used in the step 1 includes, for example, water, dimethylsulfoxide, dimethylformamide, tetrahydrofuran, 1,4-dioxane, toluene, benzene, diethyl ether, ethanol, methanol and xylene. These reaction mediums may be used either alone or in combination. Of these, a mixed reaction medium comprised of toluene, ethanol and water is especially preferable in view of high reaction yield.

The cyclic azine compound of the present invention can be obtained by conducting the conventional treating procedure after completion of the step 1. If desired, the produced compound is purified by, for example, recrystallization, column chromatography or sublimation.

The compound (2), used as a raw material for producing the cyclic azine compound of the present invention in the step 1, can be produced, for example, by a process comprising a step 2 comprising the reaction scheme, illustrated below, as specifically described below in Reference Examples 6 to 8.

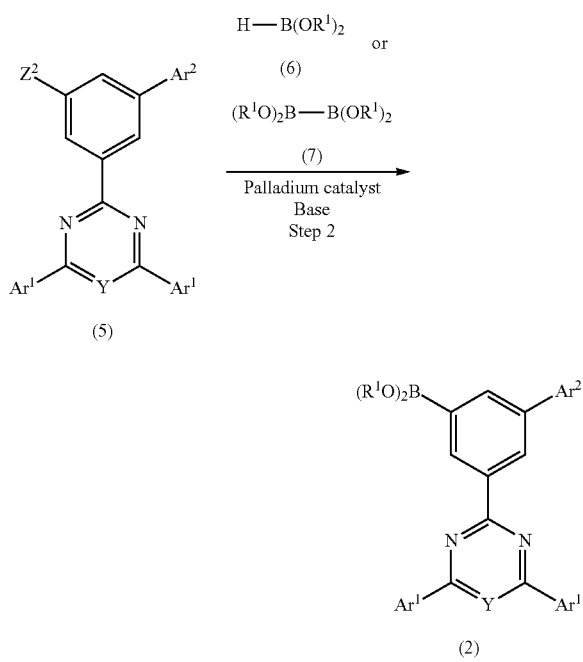

In the general formulas (5), (6), (7) and (2), Y represents C—H or a nitrogen atom; and $Ar^1$ represents an aromatic hydrocarbon group having 6 to 18 carbon atoms, which may be substituted with an alkyl group having 1 to 4 carbon atoms or a phenyl group. $Ar^2$ represents a hydrogen atom, or an aromatic hydrocarbon group having 6 to 18 carbon atoms, which may be substituted with a phenyl group or a pyridyl group, or $Ar^1$ represents a nitrogen-containing condensed ring aromatic group having 9 to 15 carbon atoms. $Z^2$ represents a leaving group. $R^1$ represents a hydrogen atom, an alkyl group having 1 to 3 carbon atoms or a phenyl group, provided that two $R^1$s in the $B(OR^1)_2$ may be the same or different, and the two $R^1$s may form a ring together with the two oxygen atoms and the boron atom.

The leaving group represented by $Z^2$ in the compound of the general formula (5) (hereinafter referred to as "compound (5)" when appropriate) is not particularly limited, and includes, for example, a chlorine atom, a bromine atom or a iodine atom. Of these, a bromine atom is preferable in view of high reaction yield.

The step 2 comprises a process of reacting compound (5) with a compound of the general formula (6) (abbreviated to "borane compound (6) when appropriate) or a compound of the general formula (7) (abbreviated to as "diboron compound (7)" when appropriate) in the presence of a palladium catalyst and a base to give compound (2) used in the step (1). This reaction can be effected with a high reaction yield of the target compound by adopting the reaction conditions disclosed in, for example, The Journal of Organic Chemistry, vol. 60, 7508-7510, 1995; or The Journal of Organic Chemistry, vol. 65, 164-168, 2000.

The palladium catalyst used in the step 2 includes, for example, palladium salts, divalent palladium complexes and zero-valent palladium complexes, and palladium complexes having a phosphine as a ligand, specific examples of which are recited above for the palladium catalyst used in the step 1. Of these, palladium complexes having tertiary phosphine as a ligand are preferable in view of high reaction yield. Especially, palladium complexes having triphenylphosphine as a ligand are more preferable in view of ease in availability and high reaction yield.

The amount of the palladium catalyst used in the step 2 may be a conventional catalytic amount and is not particularly limited, but the molar ratio of the palladium catalyst to compound (5) is preferably in the range of 1:50 to 1:10 in view of high reaction yield.

Palladium complex compounds having a tertiary phosphine as a ligand can also be synthesized in a reaction system containing a palladium salt, a divalent palladium complex or a zero-valent palladium complex, and a tertiary phosphine added therein.

As the tertiary phosphine used, there can be mentioned those which are specifically recited above in the step 1. Especially triphenylphosphine is preferable in view of ease in avalavility and reaction yield.

The molar ratio of the tertiary phosphine to the palladium salt or the palladium complex compound, used in the step 2, is not particularly limited, but is preferably in the range of 1:10 to 10:1, and more preferably 1:2 to 5:1 in view of high reaction yield.

It is essential to carry out the reaction of step 2 in the presence of a base. The base capable of being used in the step 2 includes, for example, sodium hydroxide, potassium hydroxide, sodium carbonate, potassium carbonate, lithium carbonate, cesium carbonate, potassium acetate, sodium acetate, potassium phosphate, sodium phosphate, sodium fluoride, potassium fluoride and cesium fluoride. Of these, potassium acetate is preferable in view of high reaction yield.

The molar ratio of the borane compound (6) or the diboron compound (7) to compound (5) is not particularly limited, but is preferably in the range of 1:1 to 5:1, and more preferably 2:1 to 3:1 in view of high reaction yield.

The reaction in the step 2 can be effected in a reaction medium. The reaction medium used in the step 2 includes, for example, water, dimethylsulfoxide, dimethylformamide, tetrahydrofuran, 1,4-dioxane, toluene, benzene, diethyl ether, ethanol, methanol and xylene. These reaction mediums may be used either alone or in combination. Of these, tetrahydrofuran is especially preferable in view of high reaction yield.

The compound (2) obtained in the step (2) can be either isolated after completion of the reaction, or used for the step 1 without isolation.

The cyclic azine compound of the present invention can also be produced by a process including a step 3 represented by the following reaction scheme.

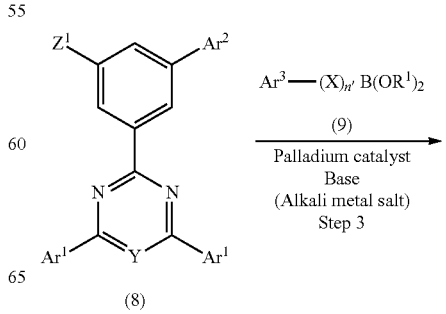

-continued

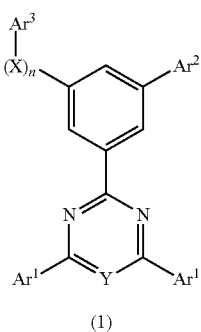

(1)

In the general formulas (8), (9) and (1), Y represents C—H or a nitrogen atom; and $Ar^1$ represents an aromatic hydrocarbon group having 6 to 18 carbon atoms, which may be substituted with an alkyl group having 1 to 4 carbon atoms or a phenyl group. $Ar^2$ represents a hydrogen atom, or an aromatic hydrocarbon group having 6 to 18 carbon atoms, which may be substituted with a phenyl group or a pyridyl group, or $Ar^2$ represents a nitrogen-containing condensed ring aromatic group having 9 to 15 carbon atoms. $R^1$ represents a hydrogen atom, an alkyl group having 1 to 3 carbon atoms or a phenyl group, provided that two $R^1$s in the $B(OR^1)_2$ may be the same or different, and the two $R^1$s may form a ring together with the two oxygen atoms and the boron atom. $Ar^3$ represents a nitrogen-containing condensed ring aromatic group having 9 to 15 carbon atoms; X represents a phenylene group; n represents an integer in the range of 0 to 3; and $Z^1$ represents a chlorine atom or a bromine atom.

The step 3 comprises a process of reacting a compound represented by the general formula (8) (abbreviated to as "compound (8)" when appropriate) with a compound of the general formula (9) (abbreviated to as "compound (9)" when appropriate) in the presence of a palladium catalyst and a base, or in the presence of a palladium catalyst, a base and an alkali metal salt to give compound (1).

The palladium catalyst used in the step 3 includes, for example, palladium salts, divalent palladium complexes and zero-valent palladium complexes, and palladium complexes having a phosphine as a ligand, specific examples of which are recited above for the palladium catalyst used in the step 1. Of these, palladium complexes having tertiary phosphine as a ligand are preferable in view of high reaction yield. Especially, palladium complexes having triphenylphosphine as a ligand are more preferable in view of ease in availability and high reaction yield.

The amount of the palladium catalyst used in the step 3 may be a conventional catalytic amount and is not particularly limited, but the molar ratio of the palladium catalyst to compound (8) is preferably in the range of 1:50 to 1:10 in view of high reaction yield.

Palladium complex compounds having a tertiary phosphine as a ligand can also be synthesized in a reaction system containing a palladium salt, a divalent palladium complex or a zero-valent palladium complex, and a tertiary phosphine added therein.

As the tertiary phosphine used, there can be mentioned those which are specifically recited above in the step 1. Especially triphenylphosphine is preferable in view of ease in avalavility and reaction yield.

The molar ratio of the tertiary phosphine to the palladium salt or the palladium complex compound, which are used in the step 3, is not particularly limited, but is preferably in the range of 1:10 to 10:1, and more preferably 1:2 to 5:1 in view of high reaction yield.

It is essential to carry out the reaction of step 3 in the presence of a base. The base capable of being used in the step 3 includes, for example, sodium hydroxide, potassium hydroxide, sodium carbonate, potassium carbonate, lithium carbonate, cesium carbonate, potassium acetate, sodium acetate, potassium phosphate, sodium phosphate, sodium fluoride, potassium fluoride and cesium fluoride. Of these, potassium carbonate is preferable in view of high reaction yield.

The molar ratio of the base to the compound (8) is not particularly limited, but is preferably in the range of 1:2 to 10:1, and more preferably 1:1 to 3:1 in view of high reaction yield.

The alkali metal salt capable of being used in the step 3 is not particularly limited and includes, for example, lithium fluoride, lithium chloride, lithium bromide, lithium iodide, sodium fluoride, sodium chloride, sodium bromide, sodium iodide, potassium fluoride, potassium chloride, potassium bromide, potassium iodide, rubidium fluoride, rubidium chloride, rubidium bromide, rubidium iodide, cesium fluoride, cesium chloride, cesium bromide and cesium iodide. Of these, lithium salts and potassium salts are preferable in view of high reaction yield and low cost. Lithium chloride and potassium chloride are especially preferable in view of very high reaction yield.

The molar ratio of the alkali metal salt to the compound (8) is not particularly limited, but is preferably in the range of 1:2 to 10:1, and more preferably 1:1 to 3:1 in view of high reaction yield.

The molar ratio of the compound (9) to the compound (8), which are used in the step 3, is not particularly limited, but is preferably in the range of 1:1 to 5:1, and more preferably 1:1 to 3:1 in view of high reaction yield.

The reaction in the step 3 can be effected in a reaction medium. The reaction medium used in the step 3 includes, for example, water, dimethylsulfoxide, dimethylformamide, tetrahydrofuran, 1,4-dioxane, toluene, benzene, diethyl ether, ethanol, methanol and xylene. These reaction mediums may be used either alone or in combination. Of these, tetrahydrofuran is especially preferable in view of high reaction yield.

The cyclic azine compound of the present invention can be obtained by conducting the conventional treating procedure after completion of the step 3. If desired, the produced compound is purified by, for example, recrystallization, column chromatography or sublimation.

Among the compounds (8) used as a raw material in the step 3 for producing the cyclic azine compound of the present invention, those wherein $Ar^2$ is other than hydrogen, i.e., $Ar^2$ represents an aromatic hydrocarbon group having 6 to 18 carbon atoms, which may be substituted with a phenyl group or a pyridyl group, or $Ar^2$ represents a nitrogen-containing condensed ring aromatic group having 9 to 15 carbon atoms, can be produced by a process comprising a step 4 comprising the reaction scheme illustrated below. The group represented by $Ar^2$ which is other than hydrogen is referred to as $Ar^{2'}$ when appropriate; and the target compound, produced by the process comprising the step 4, is referred to as "compound (8')" when appropriate.

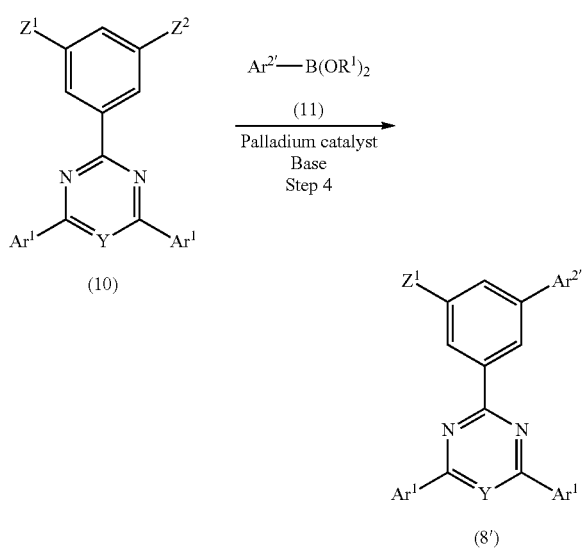

In the general formulas (10), (11) and (8'), Y represents C—H or a nitrogen atom; and Ar¹ represents an aromatic hydrocarbon group having 6 to 18 carbon atoms, which may be substituted with an alkyl group having 1 to 4 carbon atoms or a phenyl group. Ar²' represents an aromatic hydrocarbon group having 6 to 18 carbon atoms, which may be substituted with a phenyl group or a pyridyl group, or Ar²' represents a nitrogen-containing condensed ring aromatic group having 9 to 15 carbon atoms. R¹ represents a hydrogen atom, an alkyl group having 1 to 3 carbon atoms or a phenyl group, provided that two R¹s in the B(OR¹)₂ may be the same or different, and the two R¹s may form a ring together with the two oxygen atoms and the boron atom. X represents a phenylene group; n represents an integer in the range of 0 to 3; and, Z¹ and Z² represent a chlorine atom or a bromine atom.

In the process comprising the step (4), a compound represented by the general formula (10) (abbreviated to as "compound (10)" when appropriate) is reacted with a compound represented by the general formula (11) (abbreviated to as "compound (11)" when appropriate) to give the compound (8) used as a raw material in the step 3.

The palladium catalyst used in the step 4 includes, for example, palladium salts, divalent palladium complexes and zero-valent palladium complexes, and palladium complexes having a phosphine as a ligand, specific examples of which are recited above for the palladium catalyst used in the step 1. Of these, palladium complexes having tertiary phosphine as a ligand are preferable in view of high reaction yield. Especially, palladium complexes having triphenylphosphine as a ligand are more preferable in view of ease in availability and high reaction yield.

The amount of the palladium catalyst used in the step 4 may be a conventional catalytic amount and is not particularly limited, but the molar ratio of the palladium catalyst to compound (10) is preferably in the range of 1:50 to 1:10 in view of high reaction yield.

Palladium complex compounds having a tertiary phosphine as a ligand can also be synthesized in a reaction system containing a palladium salt, a divalent palladium complex or a zero-valent palladium complex, and a tertiary phosphine added therein.

As the tertiary phosphine used, there can be mentioned those which are specifically recited above in the step 1. Of these, triphenylphosphine and 2-dicyclohexylphosphino-2',4',6'-triisopropylbiphenyl is especially preferable in view of easy availability.

The molar ratio of the tertiary phosphine to the palladium salt or the palladium complex compound, used in the step 4, is not particularly limited, but is preferably in the range of 1:10 to 10:1, and more preferably 1:2 to 5:1 in view of high reaction yield.

It is essential to carry out the reaction of step 4 in the presence of a base. The base capable of being used in the step 4 includes, for example, sodium hydroxide, potassium hydroxide, sodium carbonate, potassium carbonate, lithium carbonate, cesium carbonate, potassium acetate, sodium acetate, potassium phosphate, sodium phosphate, sodium fluoride, potassium fluoride and cesium fluoride. Of these, potassium carbonate is preferable in view of high reaction yield.

The molar ratio of the base to the compound (10) is not particularly limited, but is preferably in the range of 1:2 to 10:1, and more preferably 1:1 to 3:1 in view of high reaction yield.

The molar ratio of a compound represented by the formula (11) (abbreviated to as "compound (11)" when appropriate) to the compound (8), which are used in the step 4, is not particularly limited, but is preferably in the range of 1:1 to 5:1, and more preferably 1:1 to 3:1 in view of high reaction yield.

The reaction in the step 4 can be effected in a reaction medium. The reaction medium used in the step 4 includes, for example, water, dimethylsulfoxide, dimethylformamide, tetrahydrofuran, 1,4-dioxane, toluene, benzene, diethyl ether, ethanol, methanol and xylene. These reaction mediums may be used either alone or in combination. Of these, toluene and ethanol are especially preferable in view of high reaction yield.

The compound (8') obtained in the step 4 can be either isolated, or, used in the step 3 without isolation.

The cyclic azine compound of the present invention can also be produced by a process including a step 5 represented by the reaction scheme illustrated below.

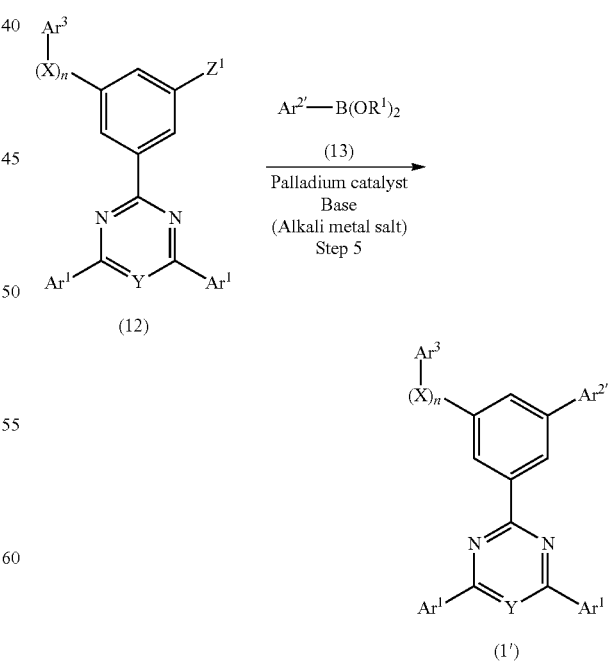

In the general formulas (12), (13) and (1'), Y represents C—H or a nitrogen atom; and Ar¹ represents an aromatic hydrocarbon group having 6 to 18 carbon atoms, which may be substituted with an alkyl group having 1 to 4 carbon atoms or a phenyl group. $Ar^2$ represents a hydrogen atom, or an aromatic hydrocarbon group having 6 to 18 carbon atoms, which may be substituted with a phenyl group or a pyridyl group, or $Ar^2$ represents a nitrogen-containing condensed ring aromatic group having 9 to 15 carbon atoms. $R^1$ represents a hydrogen atom, an alkyl group having 1 to 3 carbon atoms or a phenyl group, provided that two $R^1$s in the $B(OR^1)_2$ may be the same or different, and the two $R^1$s may form a ring together with the two oxygen atoms and the boron atom. $Ar^3$ represents a nitrogen-containing condensed ring aromatic group having 9 to 15 carbon atoms; X represents a phenylene group; n represents an integer in the range of 0 to 3; and $Z^1$ represents a chlorine atom or a bromine atom.

The step 5 comprises a process of reacting a compound represented by the general formula (12) (abbreviated to as "compound (12)" when appropriate) with a compound of the general formula (13) (abbreviated to as "compound (13)" when appropriate) in the presence of a palladium catalyst and a base, or in the presence of a palladium catalyst, a base and an alkali metal salt to give the compound (1).

The palladium catalyst used in the step 5 includes, for example, palladium salts, divalent palladium complexes and zero-valent palladium complexes, and palladium complexes having a phosphine as a ligand, specific examples of which are recited above for the palladium catalyst used in the step 1. Of these, palladium complexes having tertiary phosphine as a ligand are preferable in view of high reaction yield. Especially, palladium complexes having triphenylphosphine as a ligand are more preferable in view of ease in availability and high reaction yield.

The amount of the palladium catalyst used in the step 5 may be a conventional catalytic amount and is not particularly limited, but the molar ratio of the palladium catalyst to compound (12) is preferably in the range of 1:50 to 1:10 in view of high reaction yield.

Palladium complex compounds having a tertiary phosphine as a ligand can also be synthesized in a reaction system containing a palladium salt, a divalent palladium complex or a zero-valent palladium complex, and a tertiary phosphine added therein.

As the tertiary phosphine used, there can be mentioned those which are specifically recited above in the step 1. Of these, triphenylphosphine and 2-dicyclohexylphosphino-2',4',6'-triisopropylbiphenyl are especially preferable in view of easy availability.

The molar ratio of the tertiary phosphine to the palladium salt or the palladium complex compound, used in the step 5, is not particularly limited, but is preferably in the range of 1:10 to 10:1, and more preferably 1:2 to 5:1 in view of high reaction yield.

The alkali metal salt capable of being used in the step 5 is not particularly limited and includes, for example, lithium fluoride, lithium chloride, lithium bromide, lithium iodide, sodium fluoride, sodium chloride, sodium bromide, sodium iodide, potassium fluoride, potassium chloride, potassium bromide, potassium iodide, rubidium fluoride, rubidium chloride, rubidium bromide, rubidium iodide, cesium fluoride, cesium chloride, cesium bromide and cesium iodide. Of these, lithium chloride and potassium chloride are preferable in view of high reaction yield.

The molar ratio of the alkali metal salt to the compound (12) is not particularly limited, but is preferably in the range of 1:2 to 10:1, and more preferably 1:1 to 3:1 in view of high reaction yield.

It is essential to carry out the reaction of step 5 in the presence of a base. The base capable of being used in the step 5 includes, for example, sodium hydroxide, potassium hydroxide, sodium carbonate, potassium carbonate, lithium carbonate, cesium carbonate, potassium acetate, sodium acetate, potassium phosphate, sodium phosphate, sodium fluoride, potassium fluoride and cesium fluoride. Of these, potassium carbonate is preferable in view of high reaction yield.

The molar ratio of the base to the compound (12) is not particularly limited, but is preferably in the range of 1:2 to 10:1, and more preferably 1:1 to 3:1 in view of high reaction yield.

The molar ratio of the compound (13) to the compound (12) used in the step 5 is not particularly limited, but is preferably in the range of 1:1 to 5:1, and more preferably 1:1 to 3:1 in view of high reaction yield.

The reaction in the step 5 can be effected in a reaction medium. The reaction medium used in the step 5 includes, for example, water, dimethylsulfoxide, dimethylformamide, tetrahydrofuran, 1,4-dioxane, toluene, benzene, diethyl ether, ethanol, methanol and xylene. These reaction mediums may be used either alone or in combination. Of these, tetrahydrofuran is especially preferable in view of high reaction yield.

The cyclic azine compound of the present invention can be obtained by conducting the conventional treating procedure after completion of the step 5. If desired, the produced compound is purified by, for example, recrystallization, column chromatography or sublimation.

The compound (12), used as a raw material for producing the cyclic azine compound of the present invention in the step 5, can be produced by a process comprising a step 6 comprising the reaction scheme, illustrated below.

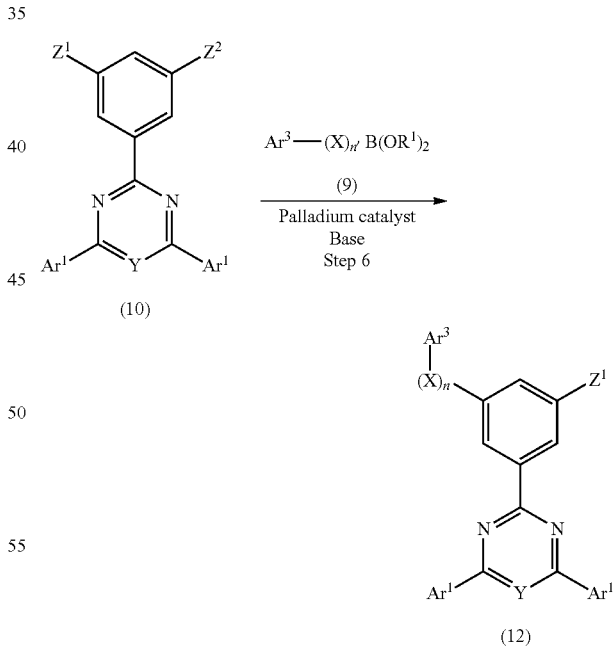

In the general formulas (10), (9) and (12), Y represents C—H or a nitrogen atom; and $Ar^1$ represents an aromatic hydrocarbon group having 6 to 18 carbon atoms, which may be substituted with an alkyl group having 1 to 4 carbon atoms or a phenyl group. $Ar^2$ represents a hydrogen atom, or an aromatic hydrocarbon group having 6 to 18 carbon atoms, which may be substituted with a phenyl group or a pyridyl group, or Ar² represents a nitrogen-containing condensed ring aromatic group having 9 to 15 carbon atoms. $R^1$ represents a hydrogen atom, an alkyl group having 1 to 3 carbon atoms or a phenyl group, provided that two $R^1$s in the $B(OR^1)_2$ may be the same or different, and the two $R^1$s may form a ring together with the two oxygen atoms and the boron atom. $Ar^3$ represents a nitrogen-containing condensed ring aromatic group having 9 to 15 carbon atoms; X represents a phenylene group; n represents an integer in the range of 0 to 3; and $Z^1$ represents a chlorine atom or a bromine atom.

The step 6 comprises a process of reacting the compound (10) with the compound (9) in the presence of a palladium catalyst and a base to give the compound (12) used in the step (5).

The palladium catalyst used in the step 6 includes, for example, palladium salts, divalent palladium complexes and zero-valent palladium complexes, and palladium complexes having a phosphine as a ligand, specific examples of which are recited above for the palladium catalyst used in the step 1. Of these, palladium complexes having tertiary phosphine as a ligand are preferable in view of high reaction yield. Especially, palladium complexes having triphenylphosphine as a ligand are more preferable in view of ease in availability and high reaction yield.

The amount of the palladium catalyst used in the step 6 may be a conventional catalytic amount and is not particularly limited, but the molar ratio of the palladium catalyst to compound (10) is preferably in the range of 1:50 to 1:10 in view of high reaction yield.

Palladium complex compounds having a tertiary phosphine as a ligand can also be synthesized in a reaction system containing a palladium salt, a divalent palladium complex or a zero-valent palladium complex, and a tertiary phosphine added therein.

As the tertiary phosphine used, there can be mentioned those which are specifically recited above in the step 1. Of these, triphenylphosphine and 2-dicyclohexylphosphino-2',4',6'-triisopropylbiphenyl are especially preferable in view of easy availability.

The molar ratio of the tertiary phosphine to the palladium salt or the palladium complex compound, used in the step 6, is not particularly limited, but is preferably in the range of 1:10 to 10:1, and more preferably 1:2 to 5:1 in view of high reaction yield.

It is essential to carry out the reaction of step 6 in the presence of a base. The base capable of being used in the step 6 includes, for example, sodium hydroxide, potassium hydroxide, sodium carbonate, potassium carbonate, lithium carbonate, cesium carbonate, potassium acetate, sodium acetate, potassium phosphate, sodium phosphate, sodium fluoride, potassium fluoride and cesium fluoride. Of these, potassium carbonate is preferable in view of high reaction yield.

The molar ratio of the base to the compound (12) is not particularly limited, but is preferably in the range of 1:2 to 10:1, and more preferably 1:1 to 3:1 in view of high reaction yield.

The molar ratio of the compound (10) to the compound (9) used in the step 6 is not particularly limited, but is preferably in the range of 1:1 to 5:1, and more preferably 1:1 to 3:1 in view of high reaction yield.

The reaction in the step 6 can be effected in a reaction medium. The reaction medium used in the step 6 includes, for example, water, dimethylsulfoxide, dimethylformamide, tetrahydrofuran, 1,4-dioxane, toluene, benzene, diethyl ether, ethanol, methanol and xylene. These reaction mediums may be used either alone or in combination. Of these, tetrahydrofuran is especially preferable in view of high reaction yield.

The compound (12) obtained in the step 6 can be either isolated, or used in the step 5 without isolation.

The process for producing a thin film of the cyclic azine compound of formula (1) according to the present invention for an organic EL device is not particularly limited. For example, vacuum deposition can be adopted for the formation of the thin film. The vacuum deposition can be conducted using a conventional vacuum deposition apparatus. However, in consideration of the tact time and cost for the production of the organic EL device, the degree of vacuum at the vacuum deposition is set preferably in the range of approximately $1 \times 10^{-2}$ Pa to $1 \times 10^{-5}$ Pa, which can be achieved, for example, by the conventionally used diffusion pump, turbo-molecular pump or cryopump. The rate of vacuum deposition varies depending upon the thickness of thin film, but the deposition rate is preferably in the range of 0.005 nm/sec to 1.0 nm/sec.

The thin film of the cyclic azine compound of the invention can also be formed from a solution thereof by, for example, spin coating, ink jetting, casting or dipping using the conventional apparatus.

EXAMPLES

The invention will now be described more specifically by the following examples and test examples, but the scope of the invention is by no means limited thereto.

Reference Example 1

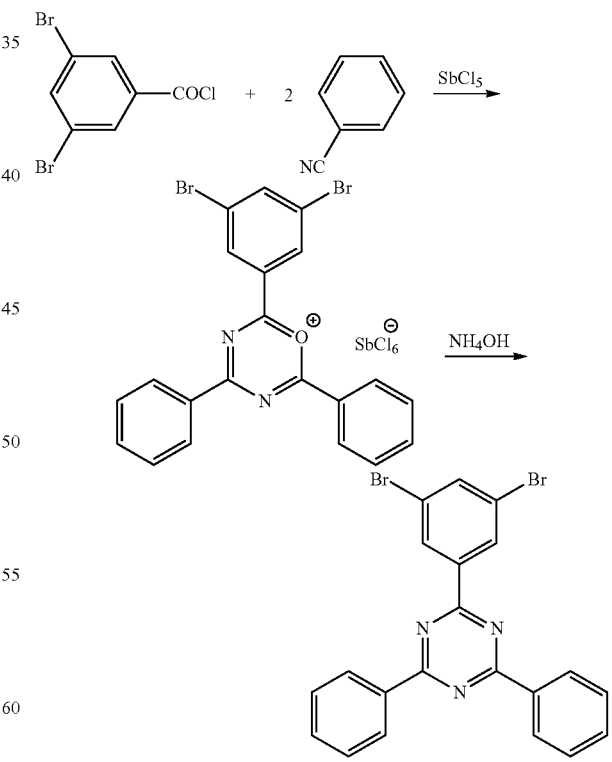

5.97 g of 3,5-dibromobenzoic acid chloride and 4.12 g of benzonitrile were dissolved in 50 mL of chloroform. The obtained solution was cooled to 0° C., and then 5.98 g of antimony pentachloride was dropwise added therein. The mixture was stirred at room temperature for 10 minutes, and then heated under reflux for 22 hours. The reaction mixture was cooled to room temperature, and then distilled under a reduced pressure thereby removing chloroform to give a yellow solid.

The yellow solid was incorporated in 300 mL of aqueous 28% ammonia, previously cooled to 0° C., to give a white solid. The white solid-containing dispersion was stirred at room temperature for one hour, and then filtered to collect the white solid. The white solid was washed with water and then with methanol. The thus-obtained white solid was purified by silica gel column chromatography to give 6.32 g of 2-(3,5-dibromophenyl)-4,6-diphenyl-1,3,5-triazine as a white solid (yield, 68%).

$^1$H-NMR (CDCl$_3$): δ7.56-7.61 (m, 4H), 7.61-7.67 (m, 2H), 7.90 (t, J=1.8 Hz, 1H), 8.72-8.78 (m, 4H), 8.82 (d, J=1.8 Hz, 2H).

$^{13}$C-NMR (CDCl$_3$): δ123.4, 128.8, 129.1, 130.6, 133.0, 135.7, 137.6, 139.8, 169.3, 172.0.

Reference Example 2

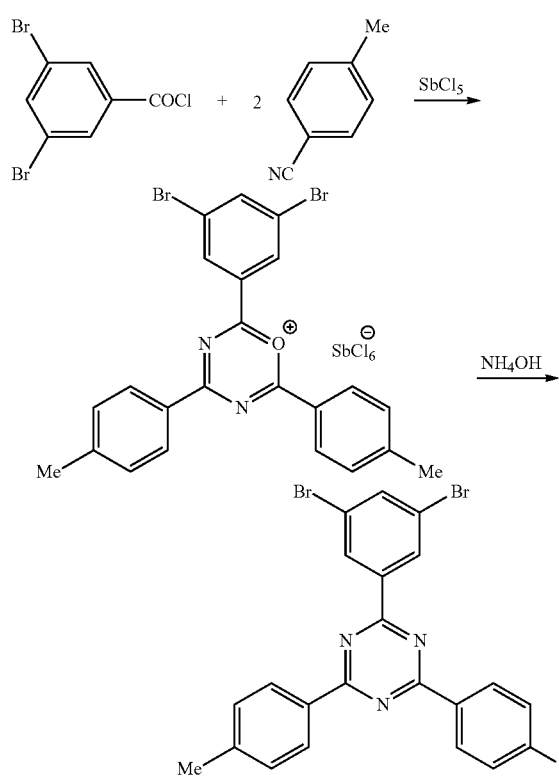

In a stream of argon, a 500 mL three-necked flask equipped with a reflux tube and a mechanical stirrer was charged with 29.8 g of 3,5-dibromobenzoic acid chloride and 23.4 g of p-tolylnitrile. 200 mL of chlorobenzene was added to the content. The thus-obtained solution was cooled to 0° C., and 29.9 g of antimony pentachloride was dropwise added therein. The mixture was stirred at room temperature for one hour, and then heated at 100° C. under reflux for 2 hours. The thus-obtained dark red suspension was cooled to −20° C., and 135 mL of aqueous 28% ammonia was added thereto. The thus-obtained white milky suspension was stirred at room temperature for 30 minutes, and then, gradually heated on an oil bath to 140° C. A solvent was removed by distillation. 100 mL of chlorobenzene was added, and the obtained suspension of the reaction mixture was heated to 130° C. and filtered to remove insoluble materials. The filtrate was left to be thereby cooled, and 100 mL of methanol was added thereto. The thus-deposited solid was collected by filtration, and washed twice with each 30 mL of methanol and then dried to give 21.2 g of target 2-(3,5-dibromophenyl)-4,6-di(p-tolyl)-1,3,5-triazine as a white powder (yield, 430). High performance liquid chromatography (HPLC) of the white powder revealed that the content of 2-(3,5-dibromophenyl)-4,6-di(p-tolyl)-1,3,5-triazine was 95.2%.

The insoluble materials removed by filtration of the heated suspension in chlorobenzene of the reaction mixture were treated by using chlorobenzene (100 mL×2) in the same manner as mentioned above. Thus, 12.9 g of 2-(3,5-dibromophenyl)-4,6-di(p-tolyl)-1,3,5-triazine was obtained as a white powder (yield, 26%). HPLC of the white powder revealed that the content of 2-(3,5-dibromophenyl)-4,6-di(p-tolyl)-1,3,5-triazine was 98.50.

$^1$H-NMR (CDCl$_3$): δ2.51 (s, 6H), 7.39 (d, J=8.1 Hz, 4H), 7.90 (t, J=1.7 Hz, 1H), 8.63 (d, J=8.1 Hz, 4H), 8.80 (d, J=1.7 Hz, 2H).

$^{13}$C-NMR (CDCl$_3$): δ22.5 (CH3×2), 123.3 (quart.×2), 129.1 (CH×4), 129.5 (CH×4), 130.6 (CH×2), 133.1 (quart.× 2), 137.4 (CH), 140.0 (quart.), 143.6 (quart.×2), 169.0 (quart.), 171.8 (quart.×2).

Reference Example 3

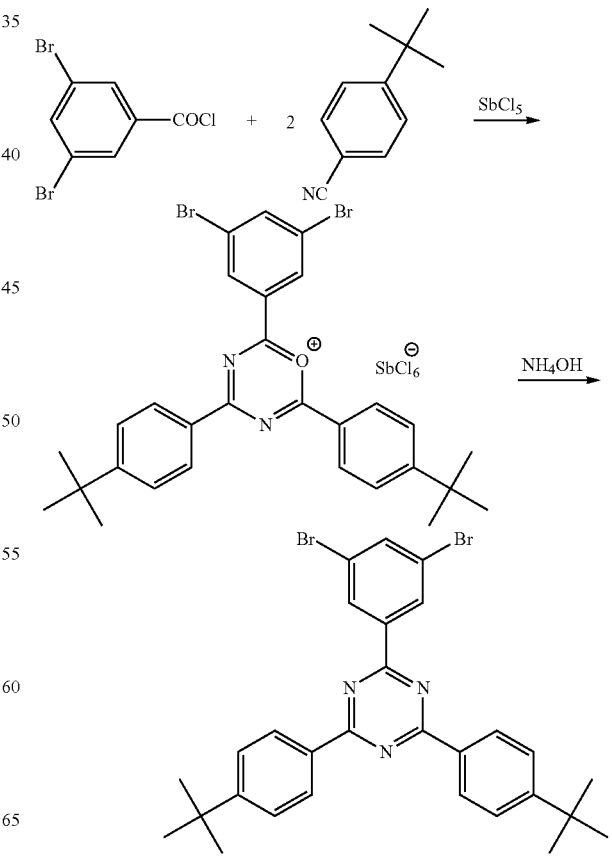

2.98 g of 3,5-dibromobenzoic acid chloride and 3.18 g of 4-tert-butylbenzonitrile were dissolved in 30 mL of chloroform. The obtained solution was cooled to 0° C., and then 2.99 g of antimony pentachloride was dropwise added therein. The mixture was stirred at room temperature for 10 minutes, and then heated under reflux for 17 hours. The reaction mixture was cooled to room temperature, and then distilled under a reduced pressure to remove chloroform.

The thus-obtained solid was incorporated in 200 mL of aqueous 28% ammonia at 0° C. to give a white solid. The white solid-containing dispersion was stirred at room temperature for one hour, and then filtered to collect the white solid. The white solid was washed with water and then with methanol. The thus-obtained white solid was purified by silica gel column chromatography to give 4.46 g of 2,4-bis (4-tert-butylphenyl)-6-(3,5-dibromophenyl)-1,3,5-triazine as a white solid (yield, 77%).

$^1$H-NMR (CDCl$_3$): δ1.41 (s, 18H), 7.61 (d, J=8.5 Hz, 4H), 7.88 (t, J=1.8 Hz, 1H), 8.65 (d, J=8.5 Hz, 4H), 8.80 (d, J=1.8 Hz, 2H).

$^{13}$C-NMR (CDCl$_3$): δ31.2, 35.1, 123.3, 125.7, 128.9, 130.5, 133.1, 137.4, 140.0, 156.5, 169.0, 171.8.

Reference Example 4

The thus-obtained red solid was pulverized in a stream of argon and the resultant powder was incorporated in 200 mL of aqueous 28% ammonia, previously cooled to 0° C. The thus-obtained suspension was stirred at room temperature for one hour, and then filtered to collect a solid. The solid was washed with water and then with methanol. The thus-washed solid was dried and then extracted by a Soxhlet's extractor using chloroform as extraction solvent. The liquid extract was left to stand to room temperature, and then filtered to collect a solid. The solid was dried to give 2.80 g of 2,4-di(3-biphenylyl)-6-(3,5-dibromophenyl)-1,3,5-triazine as a white powder (yield, 33%).

$^1$H-NMR (CDCl$_3$): δ7.46 (brt, J=7.4 Hz, 2H), 7.52-7.58 (m, 4H), 7.67 (dd, J=7.8 Hz, 7.7 Hz, 2H), 7.76 (brd, J=7.7 Hz, 4H), 7.86 (d, J=7.7 Hz, 2H), 7.90 (brd, 1H), 8.72 (d, J=7.8 Hz, 2H), 8.81 (d, J=1.8 Hz, 2H), 8.95 (s, 2H).

$^{13}$C-NMR (CDCl$_3$): δ123.4, 127.4, 127.7, 127.8, 128.1, 130.7, 131.7, 136.2, 137.7, 139.7, 140.7, 141.9, 169.4, 172.0.

Reference Example 5

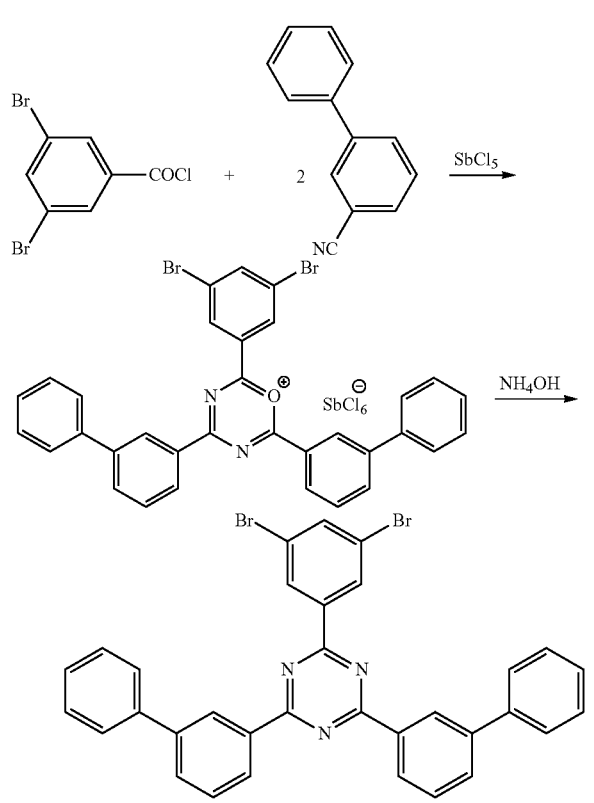

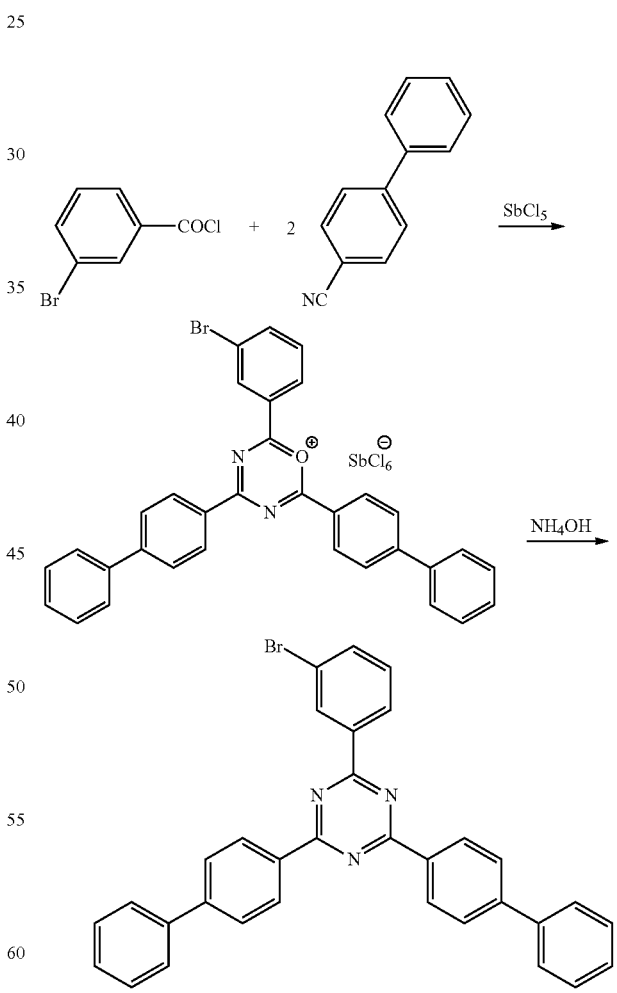

4.10 g of 3,5-dibromobenzoic acid chloride and 5.00 g of 3-biphenylcarbonitrile were dissolved in 100 mL of chloroform in a stream of argon. The thus-obtained solution was cooled to 0° C., and then 4.20 g of antimony pentachloride was dropwise added therein. The mixture was stirred at room temperature for one hour, and then heated under reflux for 12 hours. The reaction mixture was cooled to room temperature, and then distilled under a reduced pressure thereby removing low-boiling point ingredients to give a red solid.

1.9 g of 3-bromobenzoic acid chloride and 3.10 g of 4-biphenylcarbonitrile were dissolved in 50 mL of chlorobenzene in a stream of argon. The thus-obtained solution was cooled to 0° C., and then 2.59 g of antimony pentachloride was dropwise added therein. The mixture was stirred at room temperature for one hour, and then heated at 100° C. for 2 hours. The reaction mixture was left to be cooled to room temperature, and further to −20° C. Aqueous 28% ammonia was added therein to give a white precipitate. The white precipitate-containing suspension was stirred overnight at room temperature. The thus-deposited solid was collected by filtration and washed with methanol. The thus-washed solid was dried and then extracted by a Soxhlet's extractor using chloroform as extraction solvent to give 2.00 g of 2,4-di(4-biphenylyl)-6-(3-bromophenyl)-1,3,5-triazine as a white powder (yield, 43%).

$^1$H-NMR (CDCl$_3$): δ7.42 (t, J=7.4 Hz, 2H), 7.47 (t, J=7.9 Hz, 1H), 7.51 (t, J=7.2 Hz, 4H), 7.72 (d, J=7.0 Hz, 4H), 7.75 (d, J=7.9 Hz, 1H), 7.82 (d, J=8.5 Hz, 4H), 8.74 (d, J=7.9 Hz, 1H), 8.85 (d, J=8.5 Hz, 4H), 8.93 (t, J=1.8 Hz, 1H).

Reference Example 6

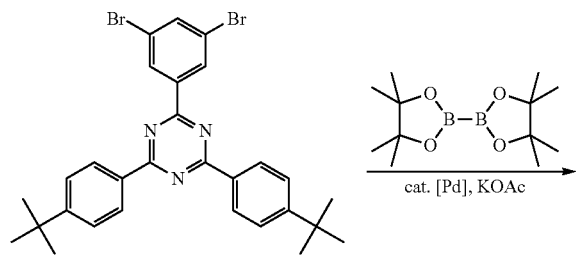

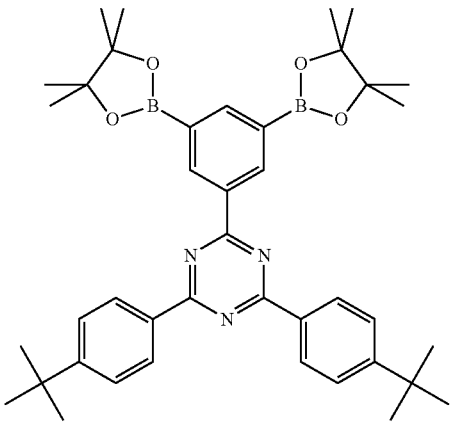

In a stream of argon, 195 mg of 2,4-bis(4-tert-butylphenyl)-6-(3,5-dibromophenyl)-1,3,5-triazine, 188 mg of bispinacolatodiboron, 159 mg of potassium acetate and 9.5 mg of bis(triphenylphosphine) palladium dichloride were suspended in 10 mL of tetrahydrofuran, and the mixture was heated under reflux for 38 hours. The reaction mixture was left to be cooled to room temperature, and then distilled under a reduced pressure to remove low-boiling point ingredients. The thus-obtained crude product was purified by silica gel column chromatography using chloroform as a developing solvent, and then washed with hexane to give 170 mg of target 2-[3,5-bis(4,4,5,5-tetramethyl-1,3,2-dioxaborolan-2-yl)phenyl]-4,6-bis(4-tert-butylphenyl)-1,3,5-triazine as a yellow solid (yield, 75%).

$^1$H-NMR (CDCl$_3$): δ1.43 (s, 18H), 1.44 (s, 24H), 7.64 (d, J=8.6 Hz, 4H), 8.52 (t, J=1.2 Hz, 1H), 8.74 (d, J=8.6 Hz, 4H), 9.23 (d, J=1.2 Hz, 2H).

Reference Example 7

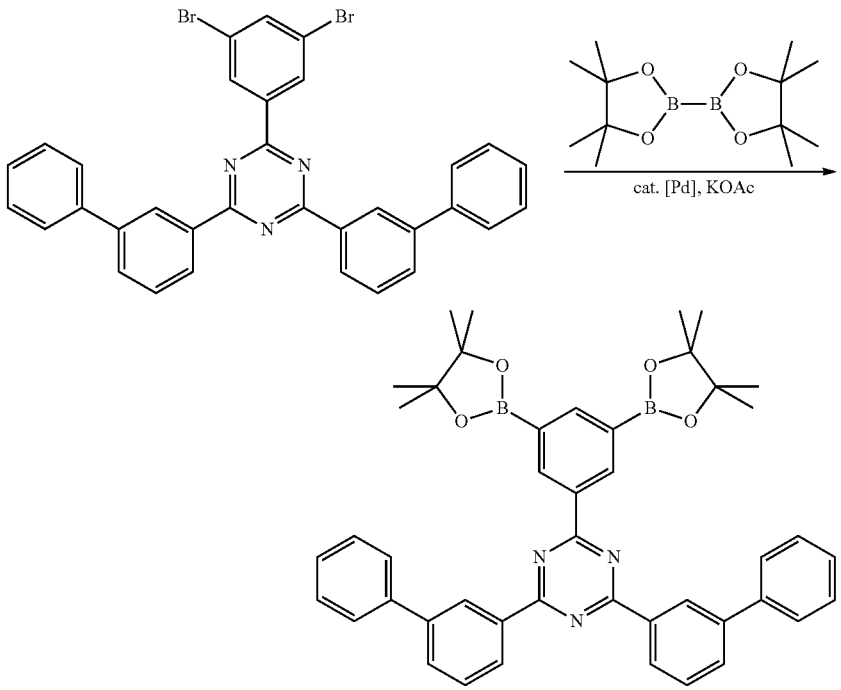

In a stream of argon, 10.0 g of 2,4-di(3-biphenylyl)-6-(3,5-dibromophenyl)-1,3,5-triazine, 9.02 g of bispinacolatodiboron, 7.00 g of potassium acetate and 453 mg of bis(triphenylphosphine)palladium dichloride were suspended in 226 mL of tetrahydrofuran, and the mixture was heated under reflux for 18 hours. The reaction mixture was left to be cooled to room temperature, and then distilled under a reduced pressure to remove low-boiling point ingredients. Water was added to the thus-obtained residue, and a deposited solid was collected by filtration. Then the collected solid was dried under a reduced pressure and purified by silica gel column chromatography using chloroform as a developing solvent to give 10.6 g of target 2,4-di(3-biphenylyl)-6-[3,5-bis(4,4,5,5-tetramethyl-1,3,2-dioxaborolan-2-yl)phenyl]-1,3,5-triazine as a white powder (yield, 92%).

$^1$H-NMR (CDCl$_3$): δ1.41 (s, 24H), 7.42 (t, J=7.4 Hz, 2H), 7.52 (t, J=7.6 Hz, 4H), 7.68 (t, J=7.8 Hz, 2H), 7.80 (d, J=7.0 Hz, 4H), 7.87 (d, J=8.4 Hz, 2H), 8.52 (t, J=1.2 Hz, 1H), 8.81 (d, J=7.9 Hz, 2H), 9.09 (t, J=1.6 Hz, 2H), 9.29 (d, J=1.3 Hz, 2H).

Reference Example 8

$^1$H-NMR (CDCl$_3$): δ1.43 (s, 12H), 7.42 (t, J=7.3 Hz, 2H), 7.51 (t, J=7.5 Hz, 4H), 7.61 (t, J=7.6 Hz, 1H), 7.73 (d, J=7.0 Hz, 4H), 7.83 (d, J=8.5 Hz, 4H), 8.07 (d, J=7.3 Hz, 1H), 8.89 (d, J=8.5 Hz, 4H), 8.90 (d, J=6.0 Hz, 1H), 9.17 (s, 1H).

Example 1

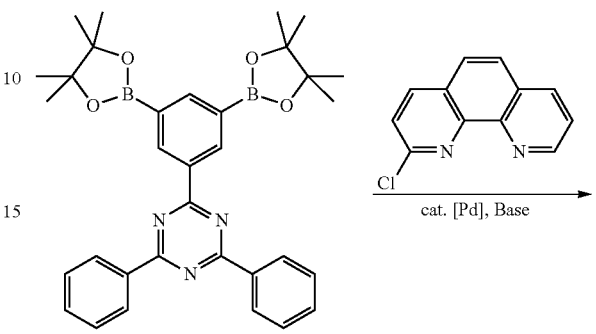

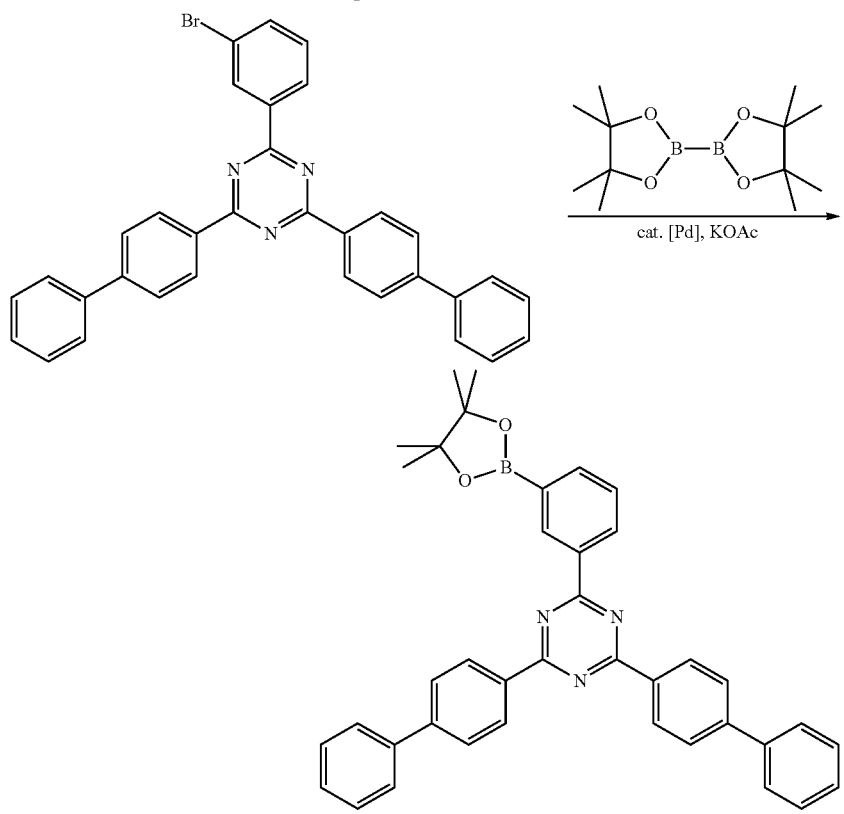

In a stream of argon, 2.16 g of 2,4-di(4-biphenylyl)-6-(3-bromophenyl)-1,3,5-triazine, 1.12 g of bispinacolatodiboron, 864 mg of potassium acetate and 70 mg of bis(triphenylphosphine)palladium dichloride were suspended in 56 mL of tetrahydrofuran, and the mixture was heated under reflux for 18 hours. The reaction mixture was left to be cooled to room temperature, and then distilled under a reduced pressure to remove low-boiling point ingredients. A water/methanol (50/50) mixed solvent was added to the thus-obtained residue, and a deposited solid was collected by filtration. Then the collected solid was dried under a reduced pressure and purified by silica gel column chromatography using hexane/chloroform (1/3) as a developing solvent to give 1.85 g of target 2,4-di(4-biphenylyl)-6-[3-(4,4,5,5-tetramethyl-1,3,2-dioxaborolan-2-yl)phenyl]-1,3,5-triazine as a milky white powder (yield, 79%).

-continued

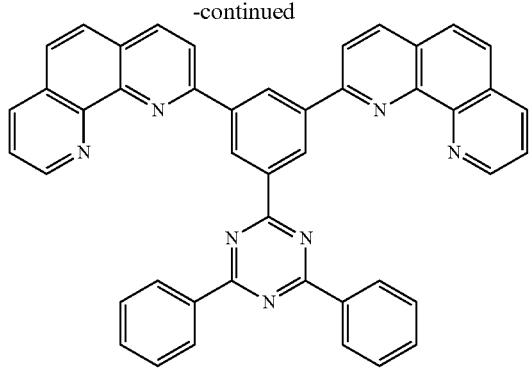

In a stream of argon, 4.26 g of 2-chloro-1,10-phenanthroline, 4.67 g 2-[3,5-bis(4,4,5,5-tetramethyl-1,3,2-dioxaborolan-2-yl)phenyl]-4,6-diphenyl-1,3,5-triazine, 1.06 g of lithium chloride and 767 mg of tetrakis(triphenylphosphine)palladium were suspended in a toluene (200 mL)/ethanol (50 mL) mixed solvent. 33.2 mL of a 2.0 M aqueous sodium carbonate solution was added in the suspension, and the mixture was stirred at 100° C. for 94 hours. Then the reaction mixture was left to be cooled to room temperature and distilled under a reduced pressure to remove low-boiling point ingredients. The obtained residue was purified by alumina column chromatography using a hexane/chloroform (1:2 to 0:1) mixed solvent as a developing solvent, and then recrystallized from a dichloromethane/methanol mixed solvent to give 4.76 g of target 2-[3,5-bis(1,10-phenanthrolin-2-yl)phenyl]-4,6-diphenyl-1,3,5-triazine as a white powder (yield, 86%).

$^1$H-NMR (CDCl$_3$): δ7.64-7.66 (m, 6H), 7.69 (dd, J=4.3, 8.0 Hz, 2H), 7.85 (d, J=8.8 Hz, 2H), 7.91 (d, J=8.8 Hz, 2H), 8.31 (dd, J=1.7, 8.0 Hz, 2H), 8.48 (d, J=8.4 Hz, 2H), 8.53 (d, J=8.4 Hz, 2H), 8.93-8.95 (m, 4H), 9.29 (dd, J=1.7, 4.3 Hz, 2H), 9.64 (t, J=1.7 Hz, 1H), 9.83 (d, J=1.7 Hz, 1H)

Example 2

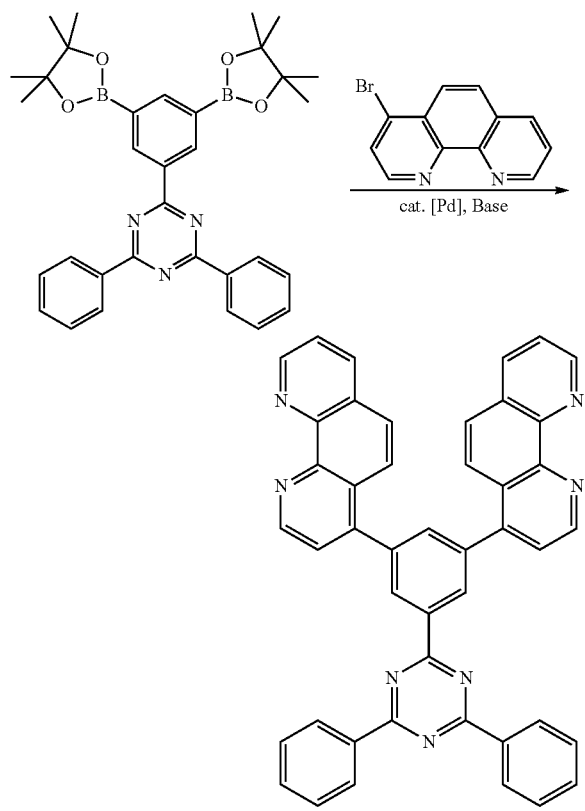

In a stream of argon, 1.42 g of 4-bromo-1,10-phenanthroline, 1.29 g 2-[3,5-bis(4,4,5,5-tetramethyl-1,3,2-dioxaborolan-2-yl)phenyl]-4,6-diphenyl-1,3,5-triazine, 515 mg of lithium chloride and 266 mg of tetrakis(triphenylphosphine)palladium were suspended in a toluene (52 mL)/ethanol (13 mL) mixed solvent. 9.2 mL of a 2.0 M aqueous sodium carbonate solution was added in the suspension, and the mixture was stirred at 100° C. for 94 hours. Then the reaction mixture was left to be cooled to room temperature and distilled under a reduced pressure to remove low-boiling point ingredients. The obtained crude product was purified by alumina column chromatography using a hexane/chloroform (1:1 to 0:1) mixed solvent as a developing solvent to give 955 mg of target 2-[3,5-bis(1,10-phenanthrolin-4-yl)phenyl]-4,6-diphenyl-1,3,5-triazine as a white powder (yield, 62%).

$^1$H-NMR (CDCl$_3$): δ7.52-7.63 (m, 6H), 7.70 (dd, J=4.4, 8.0 Hz, 2H), 7.83 (d, J=4.5 Hz, 1H), 7.85 (d, J=9.2 Hz, 1H), 7.97 (t, J=1.7 Hz, 1H), 8.09 (d, J=1.7 Hz, 1H), 8.29 (dd, J=8.1, 1.7 Hz, 2H), 8.75-8.77 (m, 4H), 9.11 (d, J=1.7 Hz, 2H), 9.27 (dd, J=4.4, 1.8 Hz, 2H), 9.35 (d, J=4.5 Hz, 2H).

Example 3

In a stream of argon, 110 mg of 4-bromo-1,10-phenanthroline, 100 mg of 2-[3,5-bis(4,4,5,5-tetramethyl-1,3,2-dioxaborolan-2-yl)phenyl]-4,6-diphenyl-1,3,5-triazine, 75.5 mg of sodium carbonate and 16.4 mg of tetrakis(triphenylphosphine)palladium were suspended in a toluene (5 mL)/ethanol (1 mL)/water (0.35 mL) mixed solvent. The mixture was stirred at 100° C. for 20 hours. Then the reaction mixture was left to be cooled to room temperature and distilled under a reduced pressure to remove low-boiling point ingredients. Water was added to the thus-obtained residue. The thus-deposited solid was collected by filtration, and washed with methanol to give a crude product containing target 2-[3,5-bis(1,10-phenanthrolin-4-yl)phenyl]-4,6-diphenyl-1,3,5-triazine. The yield of the target compound estimated by $^1$HNMR was 38%.

Example 4

The procedures described in Example 3 were repeated to obtain a crude product containing target 2-[3,5-bis(1,10-phenanthrolin-4-yl)phenyl]-4,6-diphenyl-1,3,5-triazine, wherein 98.4 mg of potassium carbonate was used instead of 75.5 mg of sodium carbonate with all other procedures remaining the same. The yield of the target compound estimated by $^1$HNMR was 33%.

Example 5

The procedures described in Example 3 were repeated to obtain a crude product containing target 2-[3,5-bis(1,10-phenanthrolin-4-yl)phenyl]-4,6-diphenyl-1,3,5-triazine, wherein 52.6 mg of lithium carbonate was used instead of 75.5 mg of sodium carbonate with all other procedures remaining the same. The yield of the target compound estimated by $^1$HNMR was 13%.

Example 6

The procedures described in Example 3 were repeated to obtain a crude product containing target 2-[3,5-bis(1,10-phenanthrolin-4-yl)phenyl]-4,6-diphenyl-1,3,5-triazine, wherein 232 mg of cesium carbonate was used instead of 75.5 mg of sodium carbonate with all other procedures remaining the same. The yield of the target compound estimated by $^1$HNMR was 50%.

Example 7

The procedures described in Example 3 were repeated to obtain a crude product containing target 2-[3,5-bis(1,10-phenanthrolin-4-yl)phenyl]-4,6-diphenyl-1,3,5-triazine, wherein 41.4 mg of potassium fluoride was used instead of 75.5 mg of sodium carbonate, and the reaction time was changed to 44 hours instead of 20 hours. All other procedures remained the same. The yield of the target compound estimated by ¹HNMR was 21%.

Example 8

The procedures described in Example 3 were repeated to give 64 mg of target 2-[3,5-bis(1,10-phenanthrolin-4-yl)phenyl]-4,6-diphenyl-1,3,5-triazine as a white powder, wherein 151 mg of tripotassium phosphate was used instead of 75.5 mg of sodium carbonate, and the reaction time was changed to 44 hours instead of 20 hours. All other procedures remained the same. The yield was 54%.

Example 9

In a stream of argon, 110 mg of 4-bromo-1,10-phenanthroline, 100 mg of 2-[3,5-bis(4,4,5,5-tetramethyl-1,3,2-dioxaborolan-2-yl)phenyl]-4,6-diphenyl-1,3,5-triazine, 3.2 mg of palladium acetate, 8.3 mg of tri(tert-butyl)phosphine tetrafluoroborate and 151 mg of tripotassium phosphate were suspended in a toluene (5 mL)/ethanol (1 mL)/water (0.35 mL) mixed solvent. The mixture was stirred at 100° C. for 46 hours. Then the reaction mixture was left to be cooled to room temperature and distilled under a reduced pressure to remove low-boiling point ingredients. Water was added to the thus-obtained residue. The thus-deposited solid was collected by filtration, and washed with methanol to give a crude product containing target 2-[3,5-bis(1,10-phenanthrolin-4-yl)phenyl]-4,6-diphenyl-1,3,5-triazine. The yield of the target compound estimated by ¹HNMR was 13%.

Example 10

The procedures described in Example 9 were repeated to obtain a crude product containing target 2-[3,5-bis(1,10-phenanthrolin-4-yl)phenyl]-4,6-diphenyl-1,3,5-triazine, wherein 232 mg of cesium carbonate was used instead of 151 mg of tripotassium phosphate with all other procedures remaining the same. The yield of the target compound estimated by ¹HNMR was 9%.

Example 11

The procedures described in Example 9 were repeated to obtain a crude product containing target 2-[3,5-bis(1,10-phenanthrolin-4-yl)phenyl]-4,6-diphenyl-1,3,5-triazine, wherein 7.9 mg of 1,1'-bis(diphenylphosphino)ferrocene was used instead of 8.3 mg of tri(tert-butyl)phosphine tetrafluoroborate with all other procedures remaining the same. The yield of the target compound estimated by ¹HNMR was 17%.

Example 12

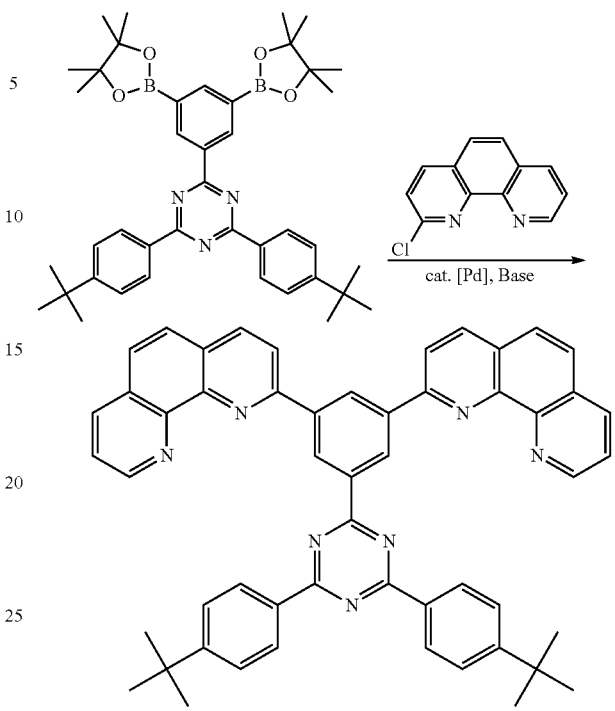

In a stream of argon, 400 mg of 2-[3,5-bis(4,4,5,5-tetramethyl-1,3,2-dioxaborolan-2-yl)phenyl]-4,6-di(4-tert-butyl)phenyl-1,3,5-triazine, 363 mg of 2-chloro-1,10-phenanthroline and 63 mg of tetrakis(triphenylphosphine) palladium were suspended in 15 mL of toluene. 7.5 mL of a 2.0 M aqueous sodium carbonate solution was added in the obtained suspension, and the mixture was stirred under reflux for 22.5 hours. Then the reaction mixture was left to be cooled to room temperature, and the thus-deposited solid was collected by filtration, and washed with water and then with methanol. The thus-obtained crude product was purified by silica gel column chromatography using a methanol/chloroform (1:100 to 1:50) mixed solvent as a developing solvent to give 359 mg of target 2-[3,5-bis(1,10-phenanthrolin-2-yl)phenyl]-4,6-di(4-tert-butylphenyl)-1,3,5-triazine as a white solid (yield, 76%).

¹H-NMR (CDCl₃): δ2.44 (s, 6H), 7.35 (d, J=8.0 Hz, 4H), 7.62 (dd, J=8.0, 4.1 Hz, 2H), 7.78 (d, J=8.8 Hz, 2H), 7.84 (d, J=8.8 Hz, 2H), 8.24 (dd, J=8.0, 1.7 Hz, 2H), 8.40 (d, J=8.3 Hz, 2H), 8.45 (d, J=8.3 Hz, 2H), 8.74 (d, J=8.0 Hz, 4H), 9.22 (dd, J=4.1, 1.6 Hz, 2H), 9.57 (t, J=1.7 Hz, 1H), 9.73 (d, J=1.7 Hz, 2H).

Example 13

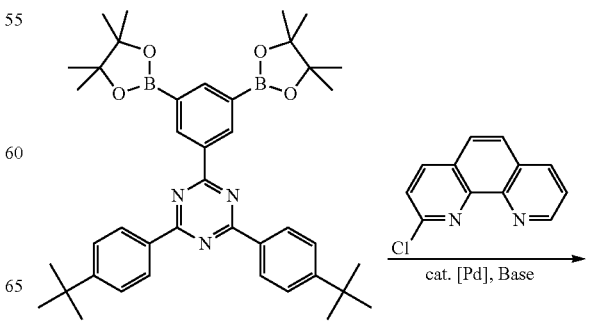

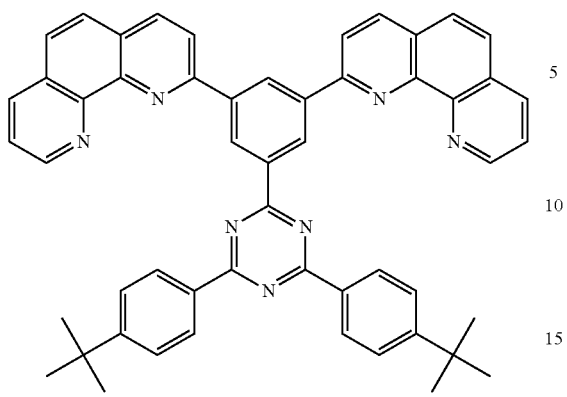

In a stream of argon, 168 mg of 2-[3,5-bis(4,4,5,5-tetramethyl-1,3,2-dioxaborolan-2-yl)-phenyl]-4,6-bis(4-tert-butylphenyl)-1,3,5-triazine, 129 mg of 2-chloro-1,10-phenanthroline, 32 mg of lithium chloride and 23 mg of tetrakis(triphenylphosphine) palladium were suspended in a toluene (6.0 mL)/ethanol (1.5 mL) mixed solvent. 1.0 mL of a 2.0 M aqueous sodium carbonate solution was added in the obtained suspension, and the mixture was stirred at 100° C. for 88 hours. Then the reaction mixture was left to be cooled to room temperature, and distilled under a reduced pressure to remove low-boiling point ingredients. Water was added to the residue to give a crude product. The crude product was collected by filtration, and evaporated to dryness under a reduced pressure. The dried crude product was recrystallized from a dichloromethane/hexane mixed solvent to give 179 mg of target 2-[3,5-bis(1,10-phenanthrolin-2-yl)phenyl]-4,6-bis(4-tert-butylphenyl)-1,3,5-triazine as a yellow solid (yield, 92%).

$^1$H-NMR (CDCl$_3$): δ1.43 (s, 18H), 7.64 (d, J=8.6 Hz, 4H), 7.68 (dd, J=8.0, 4.3 Hz, 2H), 7.84 (d, J=8.8 Hz, 2H), 7.91 (d, J=8.8 Hz, 2H), 8.30 (dd, J=8.0, 1.7 Hz, 2H), 8.46 (d, J=8.4 Hz, 2H), 8.49 (d, J=8.3 Hz, 2H), 8.82 (d, J=8.6 Hz, 4H), 9.28 (dd, J=4.3, 1.7 Hz, 2H), 9.56 (t, J=1.8 Hz, 1H), 9.76 (d, J=1.8 Hz, 2H).

Example 14

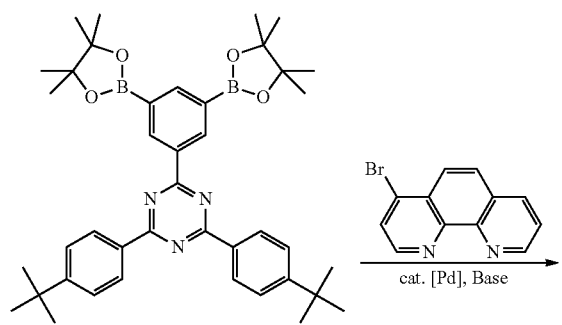

In a stream of argon, 168 mg of 2-[3,5-bis(4,4,5,5-tetramethyl-1,3,2-dioxaborolan-2-yl)-phenyl]-4,6-bis(4-tert-butylphenyl)-1,3,5-triazine, 155 mg of 4-bromo-1,10-phenanthroline, 32 mg of lithium chloride and 23 mg of tetrakis(triphenylphosphine)palladium were suspended in a toluene (6.0 mL)/ethanol (1.5 mL) mixed solvent. 1.0 mL of a 2.0M aqueous sodium carbonate solution was added in the obtained suspension, and the mixture was stirred at 100° C. for 88 hours. Then the reaction mixture was left to be cooled to room temperature, and distilled under a reduced pressure to remove low-boiling point ingredients. Water was added to the residue to give a crude product. The crude product was collected by filtration, and evaporated to dryness under a reduced pressure. The dried crude product was recrystallized from a dichloromethane/hexane mixed solvent to give 169 mg of target 2-[3,5-bis(1,10-phenanthrolin-4-yl)phenyl]-4,6-bis(4-tert-butylphenyl)-1,3,5-triazine as a white solid (yield, 87%).

$^1$H-NMR (CDCl$_3$): δ1.37 (s, 18H), 7.41 (d, J=8.5 Hz, 4H), 7.70 (dd, J=8.0, 4.3 Hz, 2H), 7.82 (d, J=4.5 Hz, 2H), 7.85 (d, J=9.3 Hz, 2H), 7.96 (s, 1H), 8.09 (d, J=9.0 Hz, 2H), 8.29 (d, J=8.2 Hz, 2H), 8.66 (d, J=8.5 Hz, 4H), 9.10 (d, J=1.4 Hz, 2H), 9.27 (dd, J=4.3, 1.6 Hz, 2H), 9.34 (d, J=4.6 Hz, 2H).

Example 15

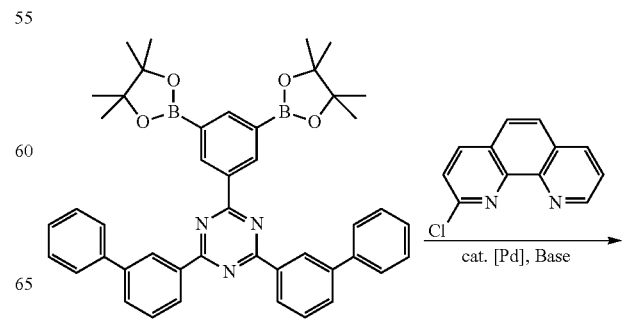

-continued

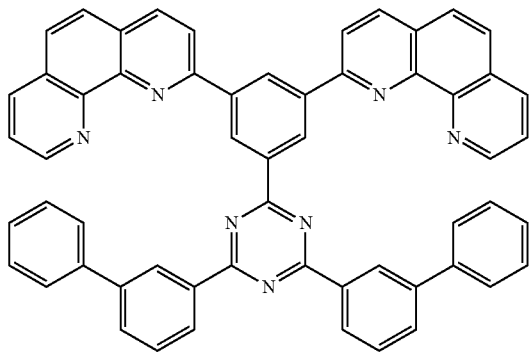

In a stream of argon, 1.13 g of 2-chloro-1,10-phenanthroline, 1.57 g of 2,4-di(3-biphenylyl-6-[3,5-bis(4,4,5,5-tetramethyl-1,3,2-dioxaborolan-2-yl)-phenyl]-1,3,5-triazine, 280 mg of lithium chloride and 203 mg of tetrakis(triphenylphosphine)palladium were suspended in a toluene (60 mL)/ethanol (15 mL) mixed solvent. 8.8 mL of a 2.0 M aqueous sodium carbonate solution was added in the obtained suspension, and the mixture was stirred at 100° C. for 65 hours. Then the reaction mixture was left to be cooled to room temperature, and distilled under a reduced pressure to remove low-boiling point ingredients. The thus-obtained residue was purified by alumina column chromatography using chloroform as a developing solvent to give 1.22 g of target 2,4-di(3-biphenylyl-6-[3,5-bis(1,10-phenanthrolin-2-yl)phenyl]-1,3,5-triazine as a white powder (yield, 68%).

$^1$H-NMR (CDCl$_3$): δ7.38-7.44 (m, 6H), 7.64 (dd, J=4.3, 8.0 Hz, 2H), 7.71 (t, J=7.7 Hz, 2H), 7.78-7.81 (m, 4H), 7.85 (d, J=8.8 Hz, 2H), 7.87 (d, J=8.3 Hz, 2H), 7.90 (d, J=8.8 Hz, 2H), 8.30 (dd, J=1.7, 8.1 Hz, 2H), 8.45 (d, J=8.4 Hz, 2H), 8.50 (d, J=8.4 Hz, 2H), 8.92 (d, J=7.8 Hz, 2H), 9.15-9.16 (m, 4H), 9.51 (t, J=1.8 Hz, 1H), 9.86 (d, J=1.7 Hz, 2H).

Example 16

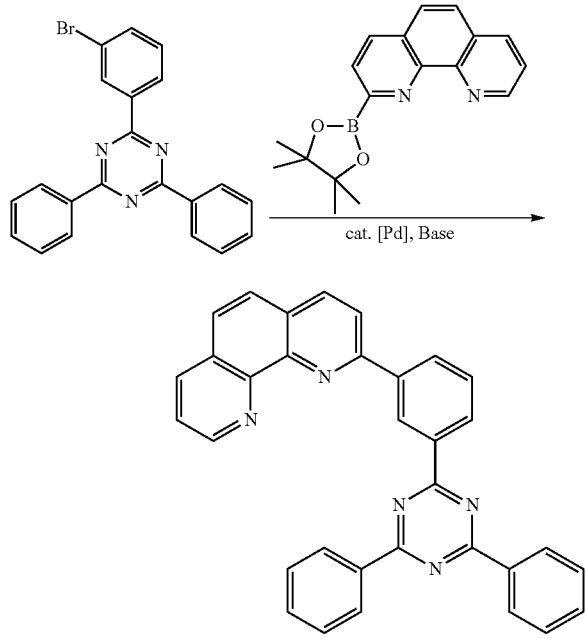

In a stream of argon, 1.20 g of 2-(3-bromophenyl)-4,6-diphenyl-1,3,5-triazine, 1.30 g of 2-(4,4,5,5-tetramethyl-1,3,2-dioxaborolan-2-yl)-1,10-phenanthroline, 1.11 g of cesium carbonate, 14 mg of palladium acetate and 32 mg of triphenylphosphine were suspended in 140 mL of tetrahydrofuran. The suspension was heated under reflux for 19 hours. Then the reaction mixture was left to be cooled to room temperature, and distilled under a reduced pressure to remove low-boiling point ingredients. Methanol was added to the residue, and the deposited solid was collected by filtration. The thus-obtained crude product was purified by silica gel column chromatography using a methanol/chloroform (1:100 to 1:77) mixed solvent as a developing solvent to give 1.37 g of target 4,6-diphenyl-2-[3-(1,10-phenanthrolin-2-yl)phenyl]-1,3,5-triazine as a white solid (yield, 91%).

$^1$H-NMR (CDCl$_3$): δ7.60-7.76 (m, 8H), 7.83 (d, J=8.8 Hz, 1H), 7.88 (d, J=8.8 Hz, 1H), 7.96-7.80 (m, 1H), 7.98 (d, J=8.4 Hz, 2H), 8.24 (d, J=8.4 Hz, 1H), 8.31 (dd, J=8.1, 1.7 Hz, 1H), 8.38 (d, J=8.4 Hz, 1H), 8.57 (d, J=8.4 Hz, 2H), 8.81-8.89 (m, 5H), 9.15 (t, J=1.6 Hz, 1H), 9.32 (dd, J=4.3, 1.7 Hz, 1H).

$^{13}$C-NMR (CDCl$_3$): δ120.9 (CH), 123.3 (CH), 126.1 (CH), 126.8 (CH), 128.1 (quart.), 128.1 (CH×2), 128.2 (CH), 128.5 (CH), 128.9 (CH×2), 129.1 (CH×4), 129.4 (CH×4), 129.5 (quart.×2), 129.6 (CH), 131.3 (CH), 133.0 (CH×2), 136.4 (quart.), 136.6 (CH), 137.3 (CH), 137.3 (quart.), 139.3 (quart.), 141.6 (quart.), 142.1 (quart.), 146.7 (quart.), 146.9 (quart.), 150.9 (CH), 157.4 (quart.), 172.0 (quart.), 172.1 (quart.×2).

Example 17

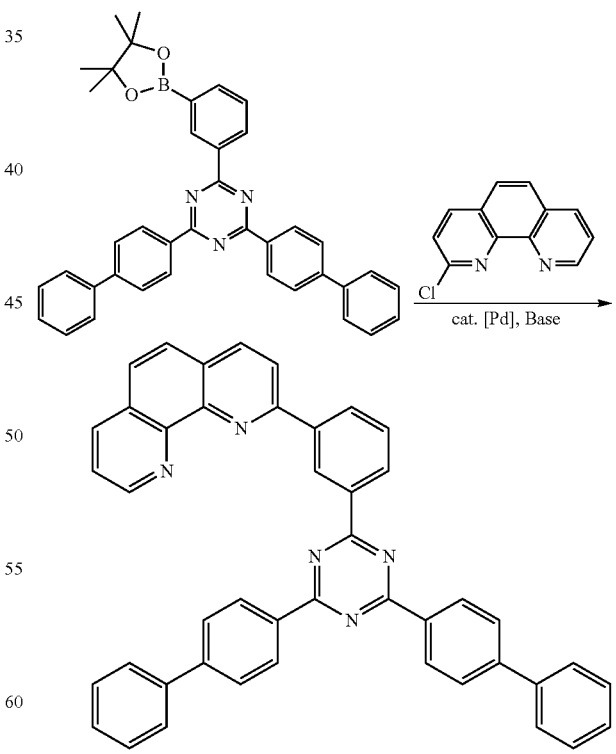

In a stream of argon, 700 mg of 2-chloro-1,10-phenanthroline, 1.60 g of 2,4-di(4-biphenylyl-6-[3-(4,4,5,5-tetramethyl-1,3,2-dioxaborolan-2-yl)phenyl]-1,3,5-triazine, 346 mg of lithium chloride and 126 mg of tetrakis(triphenylphosphine)

palladium were suspended in a toluene (64 mL)/ethanol (16 mL) mixed solvent. 5.4 mL of a 2.0 M aqueous sodium carbonate solution was added in the obtained suspension, and the mixture was stirred at 100° C. for 65 hours. Then the reaction mixture was left to be cooled to room temperature, and distilled under a reduced pressure to remove low-boiling point ingredients. The thus-obtained residue was purified by alumina column chromatography using a hexane/chloroform (1:2 to 1:3) mixed solvent as a developing solvent, and then recrystallized from a dichloromethane/methanol mixed solvent to give 1.58 g of target 2,4-di(4-biphenylyl)-6-[3-(1,10-phenanthrolin-2-yl)phenyl]-1,3,5-triazine as a white powder (yield, 91%).

$^1$H-NMR (CDCl$_3$): δ7.43 (t, J=7.3 Hz, 2H), 7.52 (t, J=7.3 Hz, 4H), 7.68 (dd, J=4.3, 8.0 Hz, 1H), 7.74 (d, J=7.1 Hz, 4H), 7.80-7.86 (m, 6H), 7.89 (d, J=8.8 Hz, 1H), 8.30 (dd, J=1.7, 8.0 Hz, 1H), 8.37 (d, J=8.4 Hz, 1H), 8.45 (d, J=8.4 Hz, 1H), 8.84 (d, J=8.0 Hz, 1H), 8.91-8.95 (m, 5H), 9.29 (dd, J=1.7, 4.3 Hz, 1H), 9.58 (t, J=1.7 Hz, 1H).

Example 18

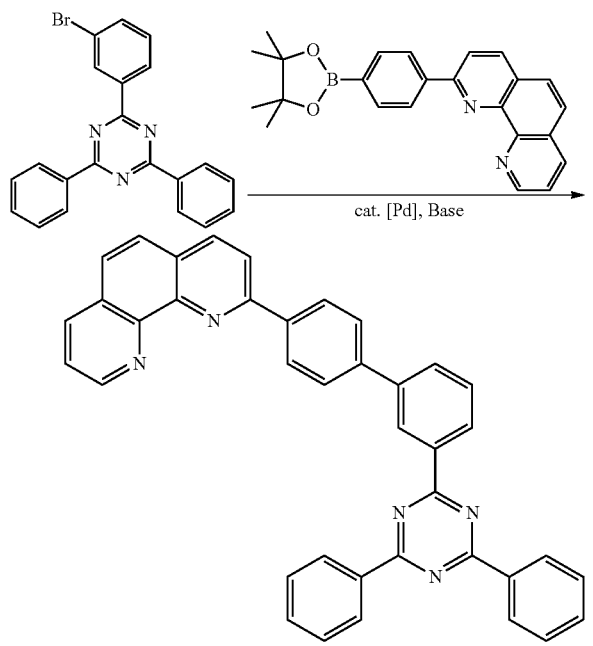

In a stream of argon, 1.20 g of 2-(3-bromophenyl)-4,6-diphenyl-1,3,5-triazine, 1.30 g of 2-[4-(4,4,5,5-tetramethyl-1,3,2-dioxaborolan-2-yl)phenyl]-1,10-phenanthroline, 1.11 g of cesium carbonate, 14 mg of palladium acetate and 32 mg of triphenylphosphine were suspended in 140 mL of tetrahydrofuran. The suspension was heated under reflux for 19 hours. Then the reaction mixture was left to be cooled to room temperature, and distilled under a reduced pressure to remove low-boiling point ingredients. Methanol was added to the residue. The thus-deposited solid was collected by filtration, and purified by silica gel column chromatography using a methanol/chloroform (1:100 to 1:77) mixed solvent as a developing solvent to give 1.37 g of target 2-[4'-(1,10-phenanthrolin-2-yl) biphenyl-3-yl]-4,6-diphenyl-1,3,5-triazine as a white solid (yield, 79%).

$^1$H-NMR (CDCl$_3$): δ7.60-7.76 (m, 8H), 7.83 (d, J=8.8 Hz, 1H), 7.88 (d, J=8.8 Hz, 1H), 7.96-7.80 (m, 1H), 7.98 (d, J=8.4 Hz, 2H), 8.24 (d, J=8.4 Hz, 1H), 8.31 (dd, J=8.1, 1.7 Hz, 1H), 8.38 (d, J=8.4 Hz, 1H), 8.57 (d, J=8.4 Hz, 2H), 8.81-8.89 (m, 5H), 9.15 (t, J=1.6 Hz, 1H), 9.32 (dd, J=4.3, 1.7 Hz, 1H).

$^{13}$C-NMR (CDCl$_3$): δ120.9 (CH), 123.3 (CH), 126.1 (CH), 126.8 (CH), 128.1 (quart.), 128.1 (CH×2), 128.2 (CH), 128.5 (CH), 128.9 (CH×2), 129.1 (CH×4), 129.4 (CH×4), 129.5 (quart.×2), 129.6 (CH), 131.3 (CH), 133.0 (CH×2), 136.4 (quart.), 136.6 (CH), 137.3 (CH), 137.3 (quart.), 139.3 (quart.), 141.6 (quart.), 142.1 (quart.), 146.7 (quart.), 146.9 (quart.), 150.9 (CH), 157.4 (quart.), 172.0 (quart.), 172.1 (quart.×2).

Example 19

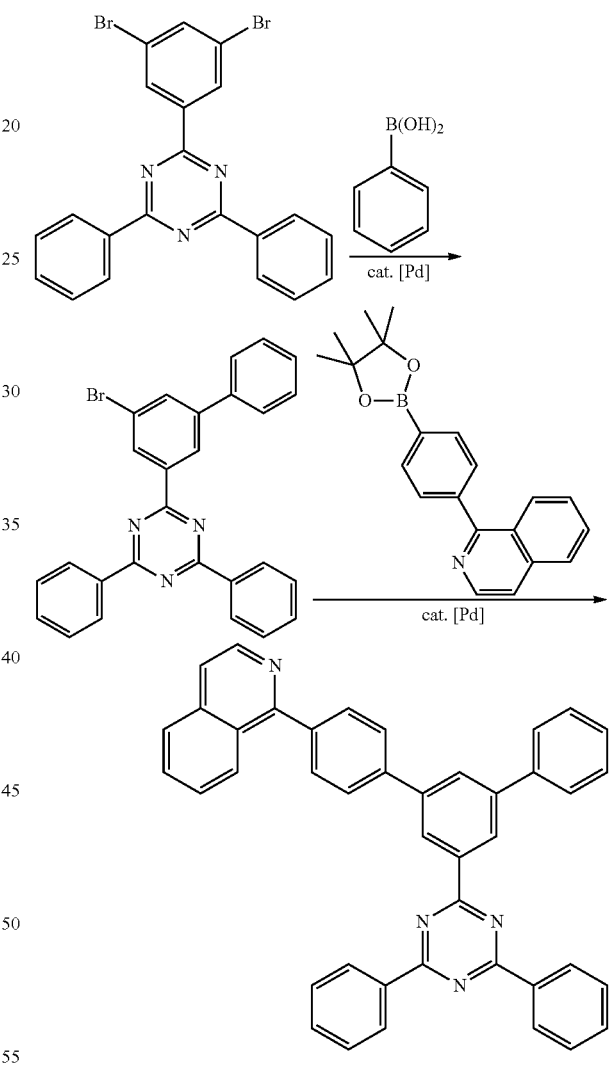

In a stream of argon, 1.00 g (2.19 mmol) of 2-(3,5-dibromophenyl)-4,6-diphenyl-1,3,5-triazine, 290 mg (2.91 mmol) of phenylboronic acid and 130 mg (0.107 mmol) of tetrakis (triphenylphosphine) palladium were suspended in a toluene (50 mL)/ethanol (50 mL) mixed solvent, and the suspension was heated to 60° C. 3.5 mL (3.53 mmol) of an aqueous 1.0 M potassium carbonate solution was gradually dropwise added to the mixture, and the mixture was stirred at that temperature for 5 hours.

Then the reaction mixture was left to be cooled to room temperature, and 1.09 g (3.29 mmol) of 1-[4-(4,4,5,5-tetramethyl-1,3,2-dioxaborolan-2-yl)phenyl]-isoquinoline was added to the reaction mixture. Then the mixture was heated to 80° C. and stirred at that temperature for 16 hours. The reaction mixture was left to be cooled to room temperature, and the deposited solid was removed by filtration. The filtrate was concentrated, and the resultant crude product was purified by silica gel column chromatography using chloroform as a developing solvent to give 682 mg of target 2-[4-(isoquinoline-1-yl)-1,1':3',1''-terphenyl-5'-yl]-4,6-diphenyl-1,3,5-triazine as a yellow crystal (yield, 54%). This compound had a melting temperature of 280° C. and a glass transition temperature of 108.1° C.

$^1$H-NMR (CDCl$_3$): δ.7.45 (t, J=7.3 Hz, 1H), 7.52-7.62 (m, 9H), 7.66 (d, J=5.5 Hz, 1H), 7.71 (t, J=7.5 Hz, 1H), 7.80-7.97 (m, 7H), 8.10 (s, 1H), 8.25 (d, J=8.5 Hz, 1H), 8.66 (d, J=5.7 Hz, 1H), 8.79 (d, J=8.2 Hz, 4H), 8.97 (s, 1H), 9.08 (s, 1H).

Example 20

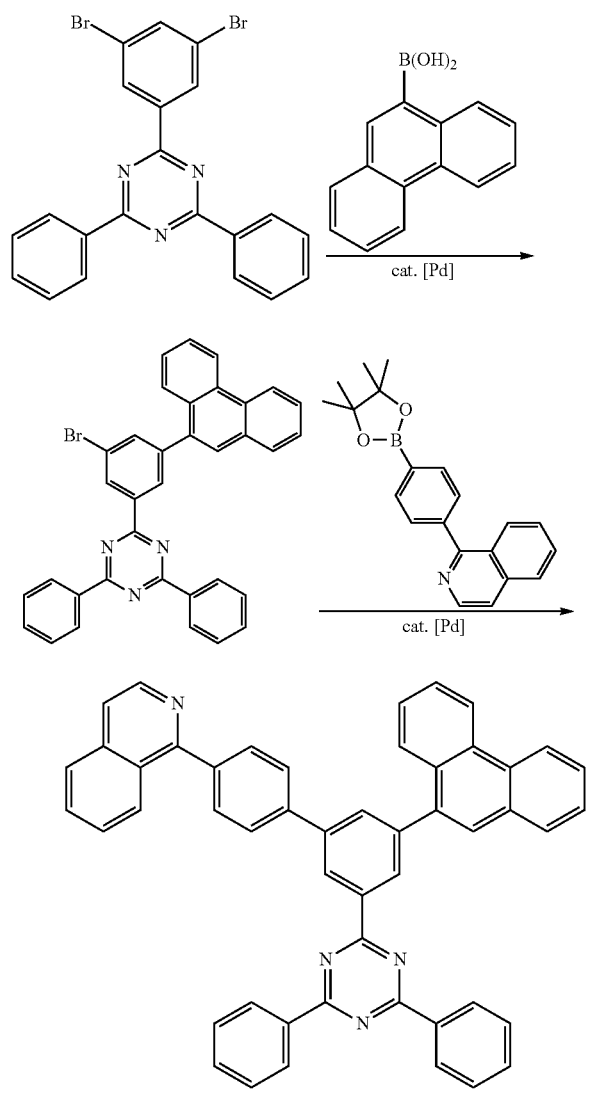

In a stream of argon, 2.00 g (4.28 mmol) of 2-(3,5-dibromophenyl)-4,6-diphenyl-1,3,5-triazine, 1.14 g (5.14 mmol) of 9-phenanthreneboronic acid and 250 mg (0.214 mmol) of tetrakis(triphenylphosphine) palladium were suspended in a toluene (88 mL)/ethanol (88 mL) mixed solvent, and the suspension was heated to 60° C. 3.5 mL (3.53 mmol) of an aqueous 1.0 M potassium carbonate solution was gradually dropwise added to the mixture, and the mixture was stirred at that temperature for 5 hours.

Then the reaction mixture was left to be cooled to room temperature, and 1.09 g (3.29 mmol) of 1-[4-(4,4,5,5-tetramethyl-1,3,2-dioxaborolan-2-yl)phenyl]-isoquinoline was added to the reaction mixture. Then the mixture was heated to 80° C. and stirred at that temperature for 16 hours. The reaction mixture was left to be cooled to room temperature, and the deposited solid was removed by filtration. The filtrate was concentrated, and the resultant crude product was purified by silica gel column chromatography using chloroform as a developing solvent to give 1.41 g of target 2-[4-(isoquinoline-1-yl)-5-(9-phenanthryl)biphenyl-3-yl]-4,6-diphenyl-1,3,5-triazine as a white crystal (yield, 48%). This compound had a melting temperature of 272° C. and a glass transition temperature of 138.8° C.

$^1$H-NMR (CDCl$_3$): δ.7.53-7.62 (m, 8H), 7.64-7.75 (m, 5H), 7.86-7.92 (m, 4H), 7.96-8.02 (m, 3H), 8.05 (d, J=8.5 Hz, 1H), 8.10 (t, J=1.8 Hz, 1H), 8.23 (d, J=8.5 Hz, 1H), 8.65 (d, J=5.7 Hz, 1H), 8.76-8.80 (m, 5H), 8.84 (d, J=8.3 Hz, 1H), 8.95 (s, 1H), 9.20 (s, 1H).

Example 21

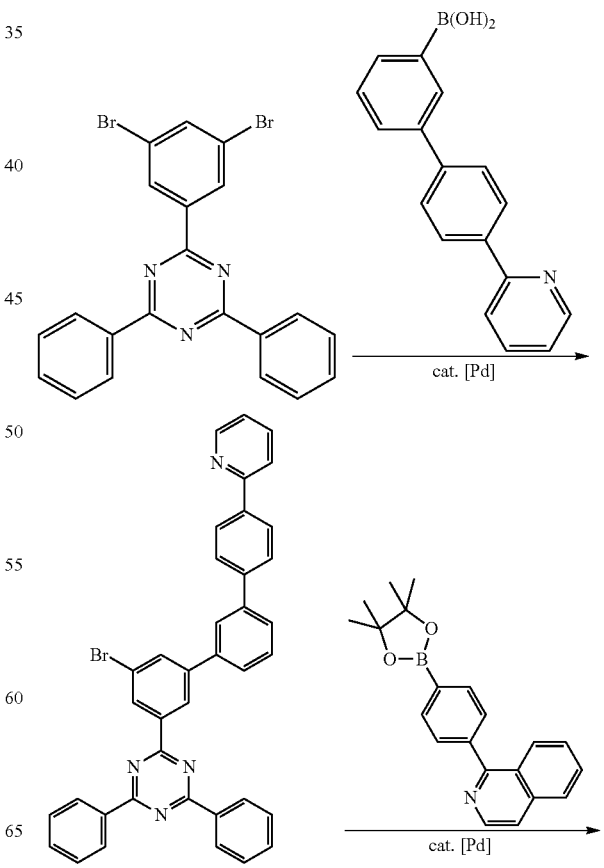

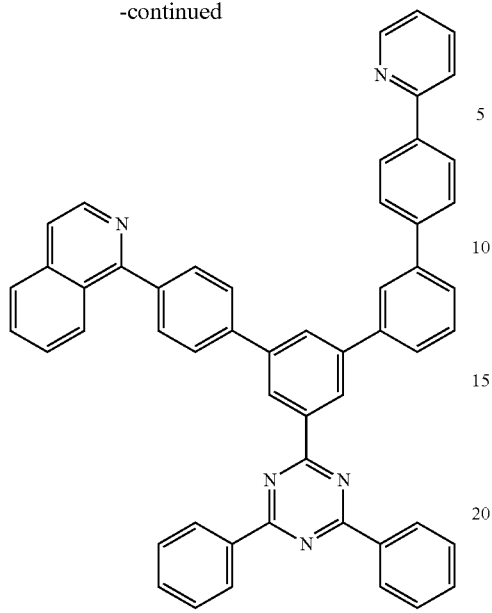

In a stream of argon, 2.89 g (6.19 mmol) of 2-(3,5-dibromophenyl)-4,6-diphenyl-1,3,5-triazine, 1.87 g (6.80 mmol) of 4'-(2-pyridyl)-3-biphenylylboronic acid and 357 mg (0.309 mmol) of tetrakis(triphenylphosphine) palladium were suspended in a toluene (100 mL)/ethanol (35 mL) mixed solvent, and the suspension was heated to 60° C. 9.3 mL (9.28 mmol) of an aqueous 1.0M potassium carbonate solution was gradually dropwise added to the mixture, and the mixture was stirred at that temperature for 5 hours.

Then the reaction mixture was left to be cooled to room temperature, and 4.10 g (12.4 mmol) of 1-[4-(4,4,5,5-tetramethyl-1,3,2-dioxaborolan-2-yl)phenyl]-isoquinoline was added to the reaction mixture. Then the mixture was heated to 80° C. and stirred at that temperature for 16 hours. The reaction mixture was left to be cooled to room temperature, and the deposited solid was removed by filtration. The filtrate was concentrated, and the resultant crude product was purified by silica gel column chromatography using chloroform as a developing solvent to give 2.07 g of target 2-[4-(isoquinoline-1-yl)-4'''-(2-pyridyl)-1,1':3',1'':3'',1'''-quaterphenyl-5'-yl]-4,6-diphenyl-1,3,5-triazine as a white solid (yield, 45%). This compound had a melting temperature of 282° C. and a glass transition temperature of 129.2° C.

$^1$H-NMR (CDCl$_3$): δ.7.56-7.64 (m, 8H), 7.65-7.70 (m, 3H), 7.72-7.82 (m, 4H), 7.84 (d, J=8.5 Hz, 2H), 7.88-7.93 (m, 3H), 7.99 (d, J=8.4 Hz, 2H), 8.07 (s, 1H), 8.13 (d, J=8.5 Hz, 2H), 8.18 (s, 1H), 8.25 (d, J=8.5 Hz, 1H), 8.65 (d, J=5.7 Hz, 1H), 8.71 (d, J=4.8 Hz, 1H), 9.03 (d, J=8.0 Hz, 4H), 9.04 (s, 1H), 9.10 (s, 1H).

Example 22

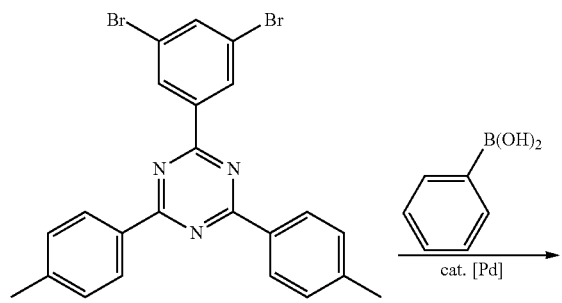

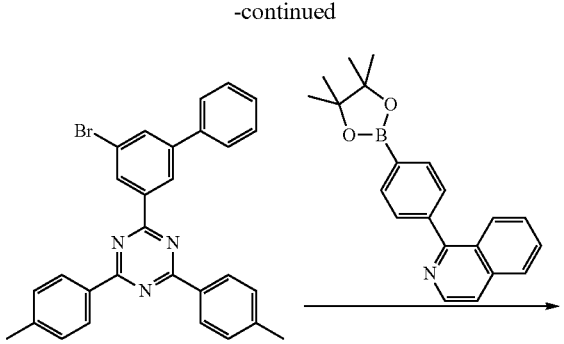

In a stream of argon, 102 mg (0.202 mmol) of 2-(3,5-dibromophenyl)-4,6-di(p-tolyl)-1,3,5-triazine, 27.1 mg (0.222 mmol) of phenylboronic acid and 27 mg (10 μmol) of tetrakis(triphenylphosphine) palladium were suspended in a toluene (4 mL)/ethanol (4 mL) mixed solvent, and the suspension was heated to 60° C. 300 μL (0.300 mmol) of an aqueous 1.0 M potassium carbonate solution was gradually dropwise added to the mixture, and the mixture was stirred at that temperature for one hour.

Then the reaction mixture was left to be cooled to room temperature, and 101 mg (0.303 mmol) of 1-[4-(4,4,5,5-tetramethyl-1,3,2-dioxaborolan-2-yl)phenyl]-isoquinoline was added to the reaction mixture. Then the mixture was heated to 80° C. and stirred at that temperature for 3 hours. The reaction mixture was left to be cooled to room temperature, and the deposited solid was removed by filtration. The filtrate was concentrated, and the resultant crude product was purified by silica gel column chromatography using chloroform as a developing solvent to give 50 mg of target 2-[4-(isoquinoline-1-yl)-1,1':3',1''-terphenyl-5'-yl]-4,6-di(p-tolyl)-1,3,5-triazine as a white solid (yield, 40%).

$^1$H-NMR (CDCl$_3$): δ.2.48 (s, 6H), 7.45 (t, J=7.3 Hz, 1H), 7.52-7.62 (m, 6H), 7.66 (d, J=5.5 Hz, 1H), 7.71 (t, J=7.5 Hz, 1H), 7.82 (d, J=7.2 Hz, 2H), 7.86-7.93 (m, 4H), 7.96 (d, J=8.3 Hz, 2H), 8.11 (s, 1H), 8.03 (t, J=1.8 Hz, 1H), 8.24 (d, J=8.3 Hz, 1H), 8.66 (d, J=8.4 Hz, 4H), 8.88 (s, 1H), 9.04 (s, 1H).

Example 23

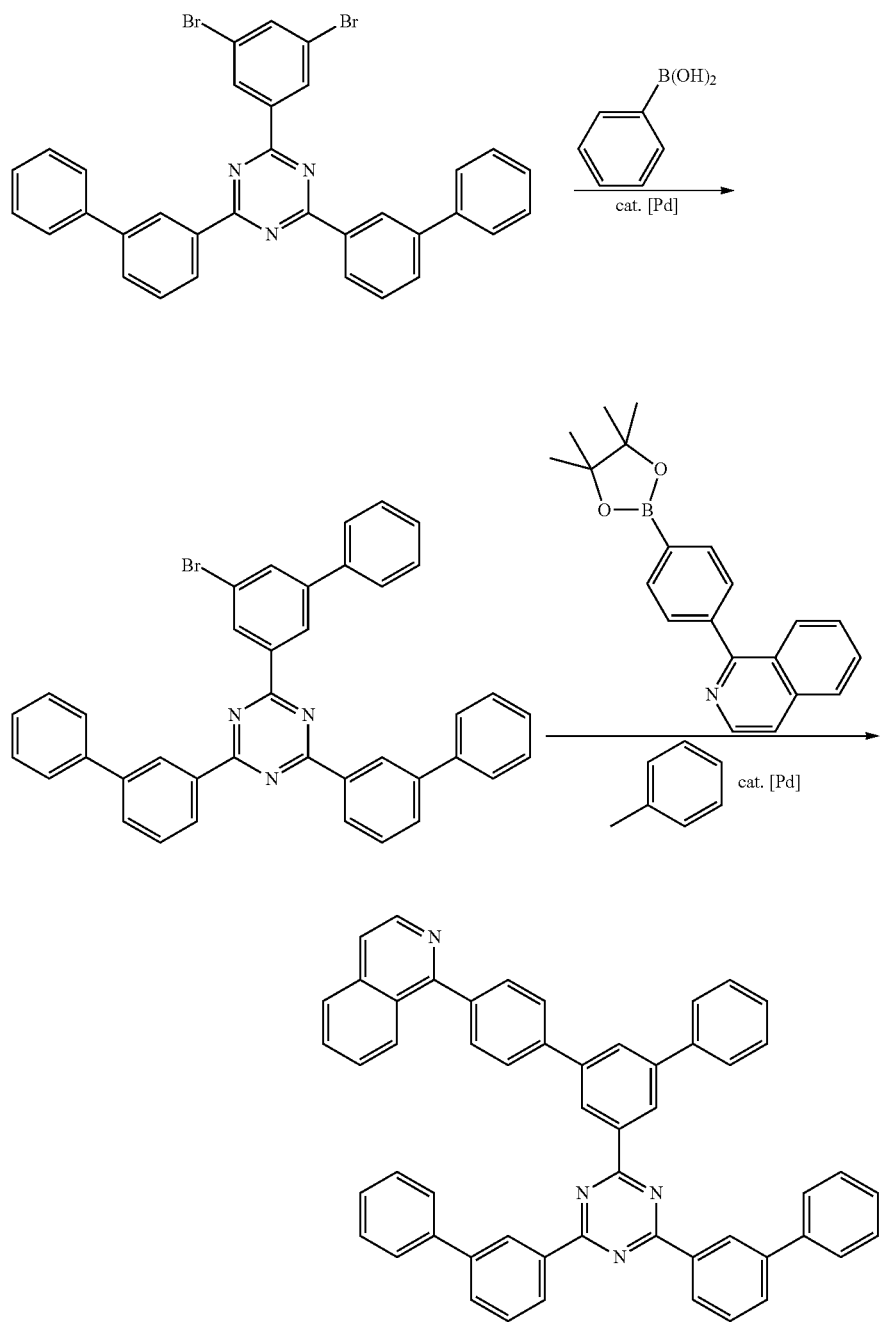

In a stream of argon, 101 mg (0.161 mmol) of 2,4-bis(3-biphenylyl)-6-(3,5-dibromophenyl)-1,3,5-triazine, 22 mg (0.178 mmol) of phenylboronic acid and 9.3 mg (8.07 µmol) of tetrakis(triphenylphosphine) palladium were suspended in a toluene (4 mL)/ethanol (4 mL) mixed solvent, and the suspension was heated to 60° C. 300 µL (0.300 mmol) of an aqueous 1.0 M potassium carbonate solution was gradually dropwise added to the mixture, and the mixture was stirred at that temperature for one hour.

Then the reaction mixture was left to be cooled to room temperature, and 80 mg (0.242 mmol) of 1-[4-(4,4,5,5-tetramethyl-1,3,2-dioxaborolan-2-yl)phenyl]-isoquinoline was added to the reaction mixture. Then the mixture was heated to 80° C. and stirred at that temperature for 3 hours. The reaction mixture was left to be cooled to room temperature, and the deposited solid was removed by filtration. The filtrate was concentrated, and the resultant crude product was purified by silica gel column chromatography using chloroform as a developing solvent to give 39 mg of target 4,6-bis(3-biphenylyl)-2-[4-(isoquinoline-1-yl)-1,1':3',1"-terphenyl-5'-yl]-1,3,5-triazine as a white solid (yield, 320).

$^1$H-NMR (CDCl$_3$): δ.7.41 (dd, J=1.8, 7.2 Hz, 2H), 7.46-7.61 (m, 8H), 7.62-7.71 (m, 5H), 7.72-7.75 (m, 3H), 7.75-7.77 (m, 2H), 7.82-7.90 (m, 6H), 7.92 (d, J=8.3 Hz, 1H), 7.98

(d, J=8.3 Hz, 1H), 8.50 (d, J=8.5 Hz, 1H), 8.65 (dd, J=5.7, 8.7 Hz, 1H), 8.41 (d, J=8.0 Hz, 4H), 9.03 (s, 1H), 9.05 (s, 1H).

Example 24

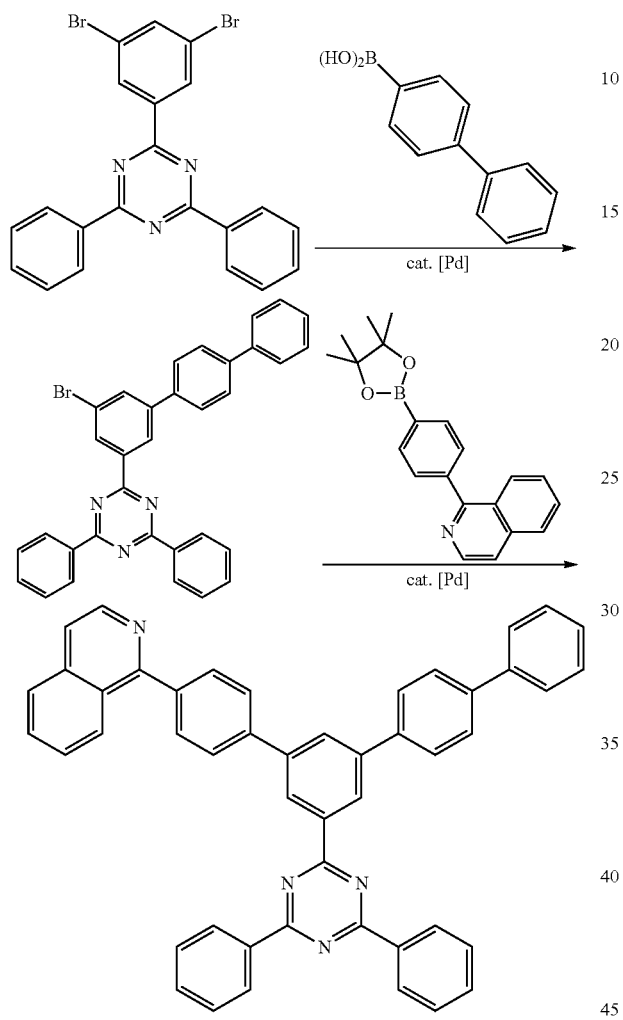

In a stream of argon, 0.500 g (1.07 mmol) of 2-(3,5-dibromophenyl)-4,6-diphenyl-1,3,5-triazine, 233 mg (1.17 mmol) of 4-biphenylylboronic acid and 61.8 mg (0.0537 mmol) of tetrakis(triphenylphosphine)palladium were suspended in a toluene (20 mL)/ethanol (6 mL) mixed solvent, and the suspension was heated to 40° C. 1.6 mL (1.61 mmol) of an aqueous 1.0 M potassium carbonate solution was gradually dropwise added to the mixture, and the mixture was stirred at that temperature for 18 hours.

Then the reaction mixture was left to be cooled to room temperature, and 0.530 g (1.61 mmol) of 1-[4-(4,4,5,5-tetramethyl-1,3,2-dioxaborolan-2-yl)phenyl]-isoquinoline was added to the reaction mixture. Then the mixture was heated to 80° C. and stirred at that temperature for 6 hours. The reaction mixture was left to be cooled to room temperature, and the deposited solid was removed by filtration. The filtrate was concentrated, and the resultant crude product was purified by silica gel column chromatography using chloroform as a developing solvent to give 430 mg of target 2-[4-(isoquinoline-1-yl)-1,1':3',":4",1'''-quaterphenyl-5'-yl]-4,6-diphenyl-1,3,5-triazine as a white crystal (yield, 60%). This compound had a melting temperature of 270° C. and a glass transition temperature of 113° C.

$^1$H-NMR (CDCl$_3$): δ.7.38 (t, J=7.4 Hz, 1H), 7.49 (t, J=7.8 Hz, 2H), 7.56-7.65 (m, 7H), 7.66-7.76 (m, 4H), 7.79 (d, J=8.5 Hz, 2H), 7.88-7.94 (m, 5H), 7.99 (d, J=8.5 Hz, 2H), 8.17 (s, 1H), 8.25 (d, J=8.5 Hz, 1H), 8.66 (d, J=5.6 Hz, 1H), 8.82 (d, J=8.2 Hz, 4H), 9.05 (s, 1H), 9.07 (s, 1H).

Example 25

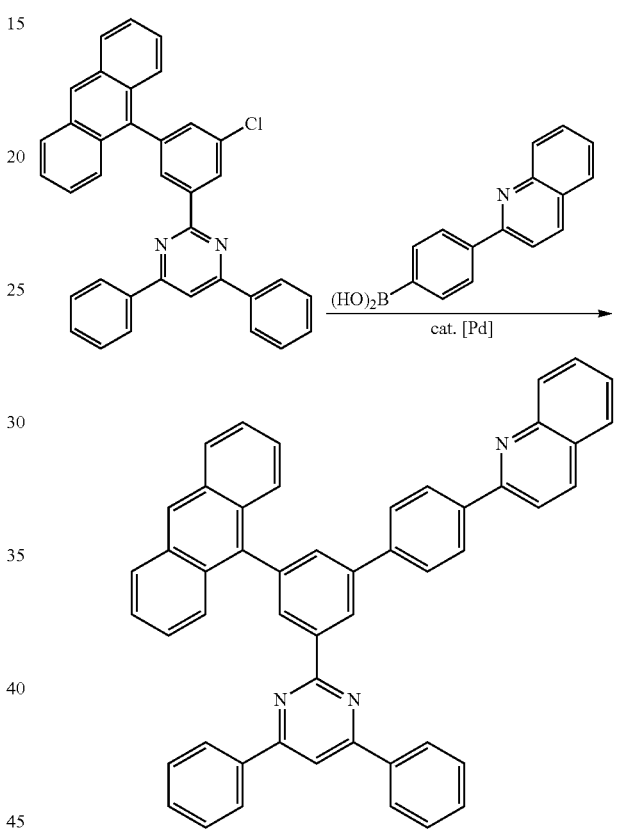

In a stream of argon, 517 mg (0.996 mmol) of 2-[5-(anthracen-9-yl)-3-chlorophenyl]-4,6-diphenylpyrimidine, 299 mg (1.20 mmol) of 4-(quinolin-2-yl)phenylboronic acid and 4.5 mg (20 μmol) of palladium acetate and 29.6 mg (60 μmol) of 2-dicyclohexylphosphino-2',4',6'-triisopropylbiphenyl were suspended in a toluene (4.5 mL)/n-butanol (0.5 mL) mixed solvent, and the suspension was heated to 95° C. 800 μL (2.40 mmol) of an aqueous 3.0M potassium carbonate solution was gradually dropwise added to the mixture, and the mixture was stirred at that temperature for 2 hours. Then the reaction mixture was left to be cooled to room temperature, and water was added to the reaction mixture. Then the deposited solid was collected by filtration to give 645 mg of target 2-[5-(anthracen-9-yl)-4'-(quinoline-2-yl) biphenyl-3-yl]-4,6-diphenylpyrimidine as a white solid (yield, 94%).

$^1$H-NMR (CDCl$_3$): δ.7.41 (d, J=6.5 Hz, 1H), 7.43 (d, J=6.5 Hz, 1H), 7.51-7.58 (m, 9H), 7.77 (t, J=7.7 Hz, 1H), 7.86 (d, J=8.0 Hz, 1H), 7.90 (d, J=8.9 Hz, 2H), 7.97 (s, 1H), 7.98 (d, J=8.6 Hz, 1H), 8.03 (d, J=8.5 Hz, 2H), 8.11 (s, 1H), 8.14 (d,

J=8.5 Hz, 2H), 8.22 (d, J=8.6 Hz, 1H), 8.26-8.32 (m, 5H), 8.35 (d, J=8.5 Hz, 2H), 8.61 (s, 1H), 8.84 (s, 1H), 9.23 (s, 1H).

Example 26

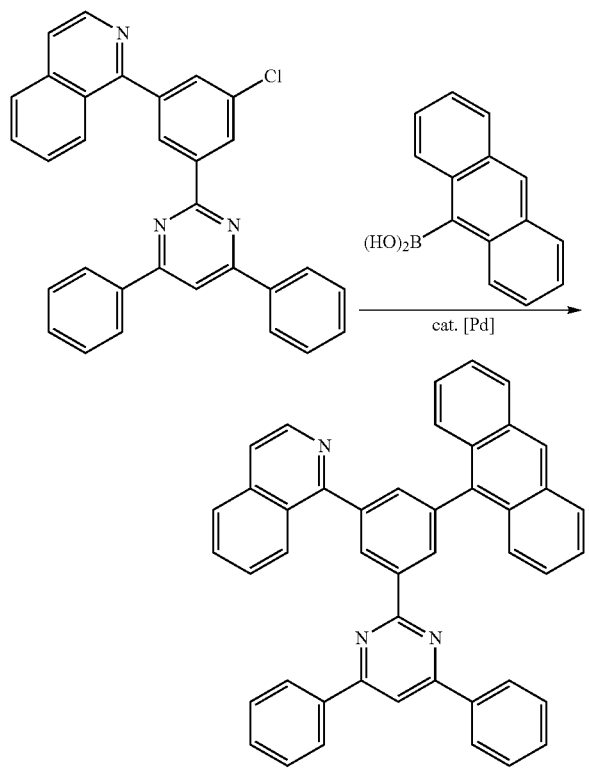

In a stream of argon, 470 mg (1.00 mmol) of 2-[5-(isoqinolin-1-yl)-3-chlorophenyl]-4,6-diphenylpyrimidine, 289 mg (1.30 mmol) of 9-anthraceneboronic acid and 4.5 mg (20 μmol) of palladium acetate and 29.6 mg (60 μmol) of 2-dicyclohexylphosphino-2',4',6'-triisopropylbiphenyl were suspended in tetrahydrofuran (5.0 mL), and the suspension was heated to 95° C. 900 μL (2.60 mmol) of an aqueous 3.0 M potassium carbonate solution was gradually dropwise added to the mixture, and the mixture was stirred at that temperature for 18 hours. Then the reaction mixture was left to be cooled to room temperature, and water was added to the reaction mixture. Then the deposited solid was collected by filtration to give 549 mg of target 2-[5-(anthracen-9-yl)-3-(isoquinoline-1-yl)phenyl]-4,6-diphenylpyrimidine as a white solid (yield, 90%).

$^1$H-NMR (CDCl$_3$): δ.7.42 (d, J=6.5 Hz, 1H), 7.44 (d, J=6.5 Hz, 1H), 7.49-7.54 (m, 8H), 7.60 (t, J=7.7 Hz, 1H), 7.72 (d, J=7.0 Hz, 1H), 7.74 (d, J=6.8 Hz, 1H), 7.93-7.95 (m, 2H), 7.97 (d, J=8.8 Hz, 2H), 8.09 (s, 1H), 8.11 (d, J=8.4 Hz, 2H), 8.26-8.29 (m, 4H), 8.37 (d, J=8.5 Hz, 1H), 8.59 (s, 1H), 8.73 (d, J=5.7 Hz, 1H), 8.99 (s, 1H), 9.30 (s, 1H).

Test Example 1

A glass substrate with an indium-tin oxide (ITO) transparent electrode was prepared, which had a stripe pattern comprised of ITO film with a 2 mm width. The substrate was washed with isopropyl alcohol and then surface-treated by irradiation of ultraviolet rays and generation of ozone. Using the surface-treated substrate, an organic electroluminescent device with an emitting area of 4 mm$^2$ having a multilayer structure as illustrated in FIG. 1 was manufactured as follows. Each layer was formed by vacuum deposition.

The glass substrate was placed in a vacuum deposition chamber, and the inner pressure was reduced to 1.0×10$^{-4}$ Pa. As illustrated in FIG. 1, organic compound layers, i.e., a hole injection layer 2, a hole transport layer 3, an emitting layer 4, a hole blocking layer 5 and an electron transport layer 6 were formed in this order on the above-mentioned glass substrate 1. Further a cathode layer 7 was formed thereon.

The hole injection layer 2 was formed by vacuum-depositing phtalocyanine copper(II), previously purified by sublimation, into a thickness of 10 nm. The hole transport layer 3 was formed by vacuum-depositing N,N'-di(1-naphthyl)-N,N'-diphenylbenzidine (NPD) into a thickness of 30 nm. The emitting layer 4 was formed by vacuum-depositing a composition comprised of 94 mass % of 4,4'-bis(carbazol-9-yl)biphenyl (CBP) and 6 mass % of tris(2-phenylpyridine)iridium (III) (Ir(ppy)$_3$) into a thickness of 30 nm.

The hole blocking layer 5 was formed by vacuum-depositing bis(2-methyl-8-quinolinolato)-(1,1'-biphenyl-4-olato)-aluminum (BAlq) into a thickness of 5 nm. The electron transport layer 6 was formed by vacuum-depositing 4,6-diphenyl-2-[3-(1,10-phenanthrolin-2-yl)phenyl]-1,3,5-triazine, synthesized in Example 16, into a thickness of 45 nm.

The vacuum deposition of each of the above-mentioned organic materials was conducted by subjecting each organic material to electric resistance heating to form a thin film at a deposition rate of 0.3 to 0.5 nm/sec.

Further a metal mask was arranged so as to be orthogonal to the ITO stripe, and thus, a cathode layer 7 was formed by vacuum-deposition. The vacuum deposition of the cathode layer 7 was conducted so as to have a double layer structure comprising a lithium fluoride layer with a thickness of 1.0 nm and an aluminum layer with a thickness of 100 nm. The measurement of thickness of each organic material thin film layer was conducted by stylus profilometer ("DEKTAK").

Finally the thus-obtained assembly of multi-layers was encapsulated with a glass cap and ultraviolet ray-curable epoxy resin (available from Nagase Chemtex Corporation). The encapsulation was conducted in a nitrogen atmosphere having an oxygen-and-moisture content of below 1 ppm within a glove box.

Luminous properties of the thus-manufactured organic EL device were evaluated by applying a direct current using a luminance meter BM-9 available from TOPCON Corporation. The luminous properties as measured at a current density of 5 mA/cm$^2$ were as follows. Voltage 6.4 V, luminance 1,545 cd/m$^2$, current efficiency 29.5 cd/A, power efficiency 14.5 lm/W. Luminance half-life of the device as measured at an initial luminance of 4,000 cd/m$^2$ was 272 hours.

Test Example 2

By the same procedures as described in Test Example 1, an organic EL device was manufactured except that an electron transport layer 6 was formed by vacuum depositing 2-[3,5-bis(1,10-phenanthrolin-2-yl)phenyl]-4,6-diphenyl)-1,3,5-triazine, synthesized in Example 1, into a thickness of 45 nm, instead of the azine compound synthesized in Example 16.

The luminous properties of thus-manufactured organic EL device as measured at a current density of 5 mA/cm$^2$ were as follows. Voltage 6.2 V, luminance 1,364 cd/m$^2$, current efficiency 30.3 cd/A and power efficiency 15.3 lm/W. Luminance half-life of the device as operated at an initial luminance of 4,000 cd/m$^2$ was 253 hours.

Test Example 3

By the same procedures as described in Test Example 1, an organic EL device was manufactured except that the multi-layer structure of the device was formed by vacuum depositing organic compounds in a manner such that a hole injection layer 2, a hole transport layer 3, an emitting layer 4 and an electron transport layer 6 were formed in this order on the glass substrate 1 as illustrated in FIG. 1, and further a cathode layer 7 was formed thereon. More specifically, the multi-layer structure of the device was carried out as follows.

The hole injection layer 2 was formed by vacuum-depositing phtalocyanine copper(II), previously purified by sublimation, into a thickness of 25 nm. The hole transport layer 3 was formed by vacuum-depositing N,N'-di(1-naphthyl)-N,N'-diphenylbenzidine (NPD) into a thickness of 45 nm.

The emitting layer 4 was formed by vacuum-depositing a composition comprised of 93 mass % of 3-tert-butyl-9,10-di(naphth-2-yl)anthracene (TBADN) and 7 mass % of 4,4'-bis[4-(di-p-tolylaminophenylethen-1-yl)biphenyl (DPAVBi) into a thickness of 40 nm. The electron transport layer 6 was formed by vacuum-depositing 2-[4-(isoquinoline-1-yl)-1,1':3',1''-terphenyl-5'-yl]-4,6-diphenyl-1,3,5-triazine, synthesized in Example 19, into a thickness of 20 nm. All other procedures and conditions remained the same as in Test Example 1.

The thus-manufactured organic EL device exhibited a voltage of 5.1 V, a luminance of 1,879 cd/m$^2$, a current efficiency of 9.4 cd/A, and a power efficiency of 5.8 lm/W, as measured at a current density of 20 mA/cm$^2$.

Test Example 4

By the same procedures as described in Test Example 3, an organic EL device was manufactured except that an electron transport layer 6 was formed by vacuum-depositing 2-[4-(isoquinoline-1-yl)-5-(9-phenanthryl)biphenyl-3-yl]-4,6-diphenyl-1,3,5-triazine, synthesized in Example 20, into a thickness of 20 nm, instead of the electron transport layer 6 formed in Test Example 3.

The thus-manufactured organic EL device exhibited a voltage of 5.6 V, a luminance of 2,030 cd/m$^2$, a current efficiency of 10.2 cd/A, and a power efficiency of 5.7 lm/W, as measured at a current density of 20 mA/cm$^2$.

Test Example 5

By the same procedures as described in Test Example 1, an organic EL device was manufactured except that the multi-layer structure of the device was formed by vacuum depositing organic compounds in a manner such that a hole injection layer 2, a hole transport layer 3, an emitting layer 4 and an electron transport layer 6 were formed in this order on the glass substrate 1 as illustrated in FIG. 1, and further a cathode layer 7 was formed thereon. More specifically, the multi-layer structure of the device was carried out as follows.

The hole injection layer 2 was formed by vacuum-depositing phtalocyanine copper(II), previously purified by sublimation, into a thickness of 25 nm. The hole transport layer 3 was formed by vacuum-depositing N,N'-di(1-naphthyl)-N,N'-diphenylbenzidine (NPD) into a thickness of 45 nm.

The emitting layer 4 was formed by vacuum-depositing a composition comprised of 95 mass % of 3-tert-butyl-9,10-di(naphth-2-yl)anthracene (TBADN) and 5 mass % of 1,6-bis(N-biphenyl-N-phenyl)pyrene into a thickness of 40 nm. The electron transport layer 6 was formed by vacuum-depositing 2-[4-(isoquinoline-1-yl)-1,1':3',1'':4'',1'''-quaterphenyl-5'-yl]-4,6-diphenyl-1,3,5-triazine, synthesized in Example 24, into a thickness of 20 nm, instead of the electron transport layer 6 in Test Example 1. All other procedures and conditions remained the same.

The thus-manufactured organic EL device exhibited a voltage of 5.8 V, a luminance of 1,386 cd/m$^2$, a current efficiency of 6.9 cd/A, and a power efficiency of 3.8 lm/W, as measured at a current density of 20 mA/cm$^2$.

Comparative Test Example 1

By the same procedures as described in Test Example 1, an organic EL device was manufactured except that an electron transport layer 6 was formed by vacuum depositing a conventional material, i.e., tris(8-quinolinolato)aluminum (III) (Alq) into a thickness of 45 nm, instead of the electron transport layer 6 in Test Example 1.

The thus-manufactured organic EL device exhibited a voltage of 7.4 V, a luminance of 1,516 cd/m$^2$, a current efficiency of 30.3 cd/A, and a power efficiency of 12.9 lm/W, as measured at a current density of 5 mA/cm$^2$. Luminance half-life of the device as operated at an initial luminance of 4,000 cd/m$^2$ was 244 hours.

Comparative Test Example 2

By the same procedures as described in Test Example 3, an organic EL device was manufactured except that an electron transport layer 6 was formed by vacuum depositing a conventional material, i.e., tris(8-quinolinolat)aluminum (III) (Alq) into a thickness of 20 nm, instead of the electron transport layer 6 in Test Example 3.

The thus-manufactured organic EL device exhibited a voltage of 6.2 V, a luminance of 1,957 cd/m$^2$, a current efficiency of 9.8 cd/A, and a power efficiency of 5.0 lm/W, as measured at a current density of 20 mA/cm$^2$.

Comparative Test Example 3

By the same procedures as described in Test Example 5, an organic EL device was manufactured except that an electron transport layer 6 was formed by vacuum depositing 2,4-diphenyl-6-[4,4''-di(2-pyridyl)-[1,1':3,1'']-terphenyl-5'-yl-1,3,5-triazine into a thickness of 20 nm, instead of the electron transport layer 6 in Test Example 5.

The thus-manufactured organic EL device exhibited a voltage of 6.4 V, a luminance of 1,279 cd/m$^2$, a current efficiency of 6.4 cd/A, and a power efficiency of 3.11 m/W, as measured at a current density of 20 mA/cm$^2$.

INDUSTRIAL APPLICABILITY

The cyclic azine compound of the present invention exhibits good electron injection and electron transport characteristics as a material for an organic EL device. Therefore, the cyclic azine compound of the present invention is useful as a material, especially an electron transport material, for an organic EL device.

An organic EL device comprising as a constituent the cyclic azine compound of the present invention is characterized as having a long life and exhibiting a low drive voltage.

The invention claimed is:
1. A cyclic azine compound represented by the formula (1):

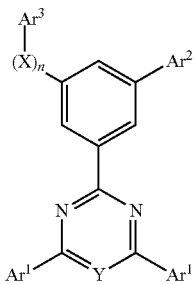

wherein,
Y represents a nitrogen atom,
Ar¹ represents an aromatic hydrocarbon group having 6 to 18 carbon atoms, which may be substituted with an alkyl group having 1 to 4 carbon atoms or a phenyl group,
Ar² represents a hydrogen atom, or an aromatic hydrocarbon group having 6 to 18 carbon atoms, which may be substituted with a phenyl group or a pyridyl group, or Ar² represents a phenanthrolinyl group, a naphthyridinyl group, a quinoxalinyl group, a phenanthridinyl group, or an acridinyl group,
Ar³ represents a quinolinyl group, an isoquinolinyl group, a phenanthrolinyl group, a naphthyridinyl group, a quinoxalinyl group, a phenanthridinyl group or an acridinyl group,
X represents a phenylene group, and
n represents an integer in the range of 0 to 3.

2. The cyclic azine compound according to claim 1, wherein Ar³ represents a phenanthrolinyl group, an isoquinolinyl group or a quinolinyl group.

3. The cyclic azine compound according to claim 1, wherein Ar² represents a hydrogen atom; a phenyl group which may be substituted with a phenyl group or a pyridyl group; a biphenylyl group which may be substituted with a phenyl group or a pyridyl group; a naphthyl group which may be substituted with a phenyl group or a pyridyl group; an anthranyl group which may be substituted with a phenyl group or a pyridyl group; a perylenyl group which may be substituted with a phenyl group or a pyridyl group; a phenanthrenyl group which may be substituted with a phenyl group or a pyridyl group; a triphenylenyl group which may be substituted with a phenyl group or a pyridyl group; a pyrenyl group which may be substituted with a phenyl group or a pyridyl group; a phenanthrolinyl group; a naphthyridinyl group; a quinoxalinyl group; a phenanthridinyl group; or an acridinyl group.

4. The cyclic azine compound according to claim 1, wherein Ar² represents a hydrogen atom, a phenyl group, a 4-biphenylyl group, a 3-biphenylyl group, a 2-biphenylyl group, a 3-(2-pyridyl)phenyl group, a 4-(2-pyridyl)phenyl group, a 1,1':4',1''-terphenyl-4-yl group, a 1,1':2',1''-terphenyl-4-yl group, a 1,1':3',1''-terphenyl-5'-yl group, a 3'-(2-pyridyl)biphenyl-3-yl group, a 3'-(3-pyridyl)biphenyl-3-yl group, a 4'-(2-pyridyl)biphenyl-4-yl group, a 4'-(3-pyridyl)biphenyl-4-yl group, a 2-naphthyl group, a 9-anthranyl group, a 9-phenanthrenyl group, a 8-(2-pyridyl)naphthanlen-2-yl group, a 10-(2-pyridyl)anthracen-9-yl group, or a phenanthrolinyl group.

5. The cyclic azine compound according to claim 1, wherein Ar¹ represents a phenyl group, a p-tolyl group, a m-tolyl group, a o-tolyl group, a 2,6-dimethylphenyl group, a 4-tert-butylphenyl group, a 4-biphenylyl group, a 3-biphenylyl group, a 2-biphenylyl group, a 1,1':4',1''-terphenyl-4-yl group, a 1,1':2',1''-terphenyl-4-yl group, a 1,1':3',1''-terphenyl-5'-yl group, a 1-naphthyl group, a 4-methylnaphthalen-1-yl group, a 4-tert-butylnaphthalen-1-yl group, a 5-methylnaphthalen-1-yl group, a 5-tert-butylnaphthalen-1-yl group, a 4-phenylnaphthalen-1-yl group, a 2-naphthyl group, a 6-methylnaphthalen-2-yl group, a 6-tert-butylnaphthalen-2-yl group, a 7-methylnaphthalen-2-yl group or a 7-tert-butylnaphthalen-2-yl group.

6. The cyclic azine compound according to claim 1, wherein Ar¹ represents a phenyl group, a p-tolyl group, a 4-tert-butylphenyl group, a 4-biphenylyl group, a 3-biphenylyl group or a 2-naphthyl group.

7. The cyclic azine compound according to claim 1, wherein n represents an integer in the range of 0, 1 or 2.

8. A process for producing a cyclic azine compound represented by the formula (1):

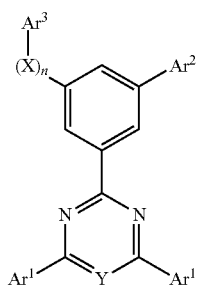

wherein,
Y represents a nitrogen atom,
Ar¹ represents an aromatic hydrocarbon group having 6 to 18 carbon atoms, which may be substituted with an alkyl group having 1 to 4 carbon atoms or a phenyl group,
Ar² represents a hydrogen atom, or an aromatic hydrocarbon group having 6 to 18 carbon atoms, which may be substituted with a phenyl group or a pyridyl group, or Ar² represents a phenanthrolinyl group, a naphthyridinyl group, a quinoxalinyl group, a phenanthridinyl group, or an acridinyl group,
Ar³ represents a quinolinyl group, an isoquinolinyl group, a phenanthrolinyl group, a naphthyridinyl group, a quinoxalinyl group, a phenanthridinyl group or an acridinyl group,
X represents a phenylene group, and
n represents an integer in the range of 0 to 3;
characterized by coupling a compound represented by the following formula (2) with a compound represented by the following formula (3) in the presence of a base and a palladium catalyst or in the presence of a base, a palladium catalyst and an alkali metal salt;

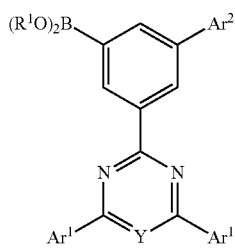
(2)

wherein,

Y represents a nitrogen atom, $Ar^1$ represents an aromatic hydrocarbon group having 6 to 18 carbon atoms, which may be substituted with an alkyl group having 1 to 4 carbon atoms or a phenyl group, $Ar^2$ represents a hydrogen atom, or an aromatic hydrocarbon group having 6 to 18 carbon atoms, which may be substituted with a phenyl group or a pyridyl group, or $Ar^2$ represents a phenanthrolinyl group, a naphthyridinyl group, a quinoxalinyl group, a phenanthridinyl group, or an acridinyl group, and $R^1$ represents a hydrogen atom, an alkyl group having 1 to 3 carbon atoms or a phenyl group, provided that two $R^1$s in the $B(OR^1)_2$ may be the same or different, and the two $R^1$s may form a ring together with the two oxygen atoms and the boron atom;

(3)

wherein, $Ar^3$ represents a quinolinyl group, an isoquinolinyl group, a phenanthrolinyl group, a naphthyridinyl group, a quinoxalinyl group, a phenanthridinyl group or an acridinyl group, X represents a phenylene group, n represents an integer in the range of 0 to 3, and $Z^1$ represents a leaving group.

9. A process for producing a cyclic azine compound represented by the formula (1):

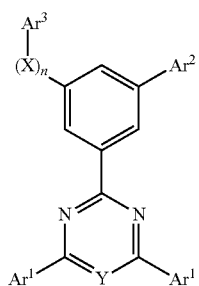
(1)

wherein,

Y represents a nitrogen atom, $Ar^1$ represents an aromatic hydrocarbon group having 6 to 18 carbon atoms, which may be substituted with an alkyl group having 1 to 4 carbon atoms or a phenyl group, $Ar^2$ represents a hydrogen atom, or an aromatic hydrocarbon group having 6 to 18 carbon atoms, which may be substituted with a phenyl group or a pyridyl group, or $Ar^2$ represents a phenanthrolinyl group, a naphthyridinyl group, a quinoxalinyl group, a phenanthridinyl group, or an acridinyl group, $Ar^3$ represents quinolinyl group, an isoquinolinyl group, a phenanthrolinyl group, a naphthyridinyl group, a quinoxalinyl group, a phenanthridinyl group or an acridinyl group, X represents a phenylene group, and n represents an integer in the range of 0 to 3;

characterized by coupling a compound represented by the following formula (8) with a compound represented by the following formula (9) in the presence of a base and a palladium catalyst or in the presence of a base, a palladium catalyst and an alkali metal salt;

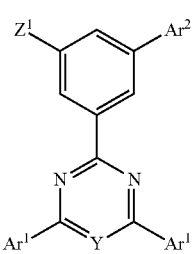
(8)

wherein,

Y represents a nitrogen atom, $Ar^1$ represents an aromatic hydrocarbon group having 6 to 18 carbon atoms, which may be substituted with an alkyl group having 1 to 4 carbon atoms or a phenyl group, $Ar^2$ represents a hydrogen atom, or an aromatic hydrocarbon group having 6 to 18 carbon atoms, which may be substituted with a phenyl group or a pyridyl group, or $Ar^2$ represents a phenanthrolinyl group, a naphthyridinyl group, a quinoxalinyl group, a phenanthridinyl group, or an acridinyl group, and $Z^1$ represents a chlorine atom or a bromine atom,

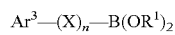
(9)

wherein, $Ar^3$ represents a quinolinyl group, an isoquinolinyl group, a phenanthrolinyl group, a naphthyridinyl group, a quinoxalinyl group, a phenanthridinyl group or an acridinyl group, X represents a phenylene group, n represents an integer in the range of 0 to 3, and $R^1$ represents a hydrogen atom, an alkyl group having 1 to 3 carbon atoms or a phenyl group, provided that two $R^1$s in the $B(OR^1)_2$ may be the same or different, and the two $R^1$s may form a ring together with the oxygen atoms and the boron atom.

10. A process for producing a cyclic azine compound represented by the formula (1'):

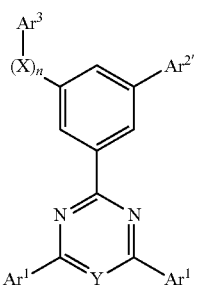
(1')

wherein,

Y represents a nitrogen atom, $Ar^1$ represents an aromatic hydrocarbon group having 6 to 18 carbon atoms, which may be substituted with an alkyl group having 1 to 4 carbon atoms or a phenyl group, $Ar^{2'}$ represents a phenanthrolinyl group, a naphthyridinyl group, a quinoxalinyl group, a phenanthridinyl group, or an acridinyl group, which may be substituted with a phenyl group or a pyridyl group, or Ar² represents a nitrogen-containing condensed ring aromatic group having 9 to 15 carbon atoms, Ar³ represents a quinolinyl group, an isoquinolinyl group, a phenanthrolinyl group, a naphthyridinyl group, a quinoxalinyl group, a phenanthridinyl group or an acridinyl group, X represents a phenylene group, and n represents an integer in the range of 0 to 3;

characterized by coupling a compound represented by the following formula (12) with a compound represented by the following formula (13) in the presence of a base and a palladium catalyst or in the presence of a base, a palladium catalyst and an alkali metal salt;

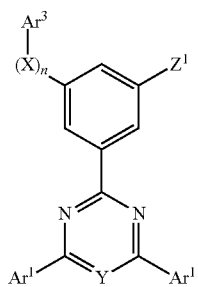

(12)

wherein,

Y represents a nitrogen atom,

Ar¹ represents an aromatic hydrocarbon group having 6 to 18 carbon atoms, which may be substituted with an alkyl group having 1 to 4 carbon atoms or a phenyl group, Ar³ represents a quinolinyl group, an isoquinolinyl group, a phenanthrolinyl group, a naphthyridinyl group, a quinoxalinyl group, a phenanthridinyl group or an acridinyl group, X represents a phenylene group, n represents an integer in the range of 0 to 3, and Z¹ represents a chlorine atom or a bromine atom;

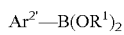 (13)

wherein,

Ar²′ represents an aromatic hydrocarbon group having 6 to 18 carbon atoms, which may be substituted with a phenyl group or a pyridyl group, or Ar²′ represents a phenanthrolinyl group; a naphthyridinyl group; a quinoxalinyl group; a phenanthridinyl group; or an acridinyl group, R¹ represents a hydrogen atom, an alkyl group having 1 to 3 carbon atoms or a phenyl group, provided that two R¹ in the B(OR¹)₂ may be the same or different, and the two R¹ may form a ring together with the two oxygen atoms and the boron atom.

11. An organic electroluminescent device which has an electron transport layer comprising, as a constituent, the cyclic azine compound as claimed in claim 1.

* * * * *

UNITED STATES PATENT AND TRADEMARK OFFICE
CERTIFICATE OF CORRECTION

PATENT NO. : 9,252,368 B2  
APPLICATION NO. : 14/357396  
DATED : February 2, 2016  
INVENTOR(S) : H. Aihara et al.

Page 1 of 1

It is certified that error appears in the above-identified patent and that said Letters Patent is hereby corrected as shown below:

Claims

Column 60, line 23 (claim 10, line 44) please change "two $R^1$" to -- two $R^1$s --

Column 60, lines 24, 25 (claim 10, lines 45, 46) please change "two $R^1$" to -- two $R^1$s --

Signed and Sealed this
Twenty-fourth Day of May, 2016

Michelle K. Lee
*Director of the United States Patent and Trademark Office*